US008747418B2

(12) United States Patent  
Qureshi et al.

(10) Patent No.: US 8,747,418 B2  
(45) Date of Patent: Jun. 10, 2014

(54) TRAJECTORY GUIDE

(75) Inventors: Salman Qureshi, Winnipeg (CA); Mark Grant, Winnipeg (CA); Genius Dacpano, Winnipeg (CA)

(73) Assignee: Monteris Medical Corporation, Plymouth, MN (US)

(*) Notice: Subject to any disclaimer, the term of this patent is extended or adjusted under 35 U.S.C. 154(b) by 594 days.

(21) Appl. No.: 12/540,500

(22) Filed: Aug. 13, 2009

(65) Prior Publication Data

US 2010/0042111 A1 Feb. 18, 2010

Related U.S. Application Data

(60) Provisional application No. 61/089,224, filed on Aug. 15, 2008, provisional application No. 61/170,859, filed on Apr. 20, 2009.

(51) Int. Cl.  
 *A61B 19/00* (2006.01)

(52) U.S. Cl.  
 USPC ........... 606/130; 600/429; 600/417; 248/168; 248/161; 248/163.1; 248/83; 606/266; 606/272

(58) Field of Classification Search  
 USPC ............... 248/168, 405; 606/130, 53, 56, 59, 606/250–258, 266, 272; 600/429, 417  
 See application file for complete search history.

(56) References Cited

U.S. PATENT DOCUMENTS 3,021,842 A * 2/1962 Flood ............................ 604/175  
3,139,990 A 7/1964 Jelatis et al.  
4,111,209 A 9/1978 Wolvek et al.  
4,609,174 A * 9/1986 Nakatani ...................... 248/465  
4,671,254 A 6/1987 Fair  
4,733,660 A 3/1988 Itzkan  
4,733,929 A 3/1988 Brown  
4,832,024 A 5/1989 Boussignac et al.  
4,914,608 A 4/1990 LeBihan et al.

(Continued)

FOREIGN PATENT DOCUMENTS

CA 1317641 5/2011  
CN 2620289 Y 6/2004

(Continued)

OTHER PUBLICATIONS

International Preliminary Report on Patentability, dated Feb. 15, 2011, regarding PCT/CA2009/001137, 8 pgs.

(Continued)

*Primary Examiner* — Katherine Dowe  
*Assistant Examiner* — Sidharth Kapoor  
(74) *Attorney, Agent, or Firm* — Oblon, Spivak, McClelland, Maier & Neustadt, L.L.P.

(57) ABSTRACT

A trajectory guide for providing access to a target site of a living subject along a desired path comprises a baseplate including a clamp lock, a guide member at least partially contained within the baseplate and having a channel therein, a plurality of adjustable legs each including a first end and a second end, wherein the first end is coupled to the baseplate, and a leg lock coupled to each adjustable leg and moveable between an unlocked position and a locked position in order to set a desired length of the adjustable leg, wherein the adjustable legs and the guide member are structured to be adjusted to provide an infinite number of trajectories in three-dimensional space extending through the channel in the guide member toward a target.

22 Claims, 18 Drawing Sheets

(56) References Cited

U.S. PATENT DOCUMENTS

| | | | |
|---|---|---|---|
| 4,986,628 A | 1/1991 | Lozhenko et al. | |
| 5,102,410 A | 4/1992 | Dressel | |
| 5,116,344 A | 5/1992 | Sundqvist | |
| 5,196,005 A | 3/1993 | Doiron et al. | |
| 5,201,742 A * | 4/1993 | Hasson | 606/130 |
| 5,207,669 A | 5/1993 | Baker et al. | |
| 5,207,681 A | 5/1993 | Ghadjar et al. | |
| 5,230,338 A | 7/1993 | Allen et al. | |
| 5,242,438 A | 9/1993 | Saadatmanesh et al. | |
| 5,246,436 A | 9/1993 | Rowe | |
| 5,247,935 A | 9/1993 | Cline et al. | |
| 5,263,956 A | 11/1993 | Nobles | |
| 5,269,777 A | 12/1993 | Doiron et al. | |
| 5,281,213 A | 1/1994 | Milder et al. | |
| 5,284,144 A | 2/1994 | Delannoy | |
| 5,291,890 A | 3/1994 | Cline et al. | |
| 5,292,320 A | 3/1994 | Brown et al. | |
| 5,307,144 A | 4/1994 | Hiroshi et al. | |
| 5,307,812 A | 5/1994 | Hardy et al. | |
| 5,320,617 A | 6/1994 | Leach | |
| 5,327,884 A | 7/1994 | Hardy et al. | |
| 5,343,543 A | 8/1994 | Novak, Jr. et al. | |
| 5,344,419 A | 9/1994 | Spears | |
| 5,354,293 A | 10/1994 | Beyer et al. | |
| 5,354,294 A | 10/1994 | Chou | |
| 5,366,456 A | 11/1994 | Rink et al. | |
| 5,368,031 A | 11/1994 | Cline et al. | |
| 5,370,649 A | 12/1994 | Gardetto et al. | |
| 5,374,266 A | 12/1994 | Kataoka et al. | |
| 5,387,220 A * | 2/1995 | Pisharodi | 606/130 |
| 5,433,717 A | 7/1995 | Rubinsky et al. | |
| 5,445,166 A | 8/1995 | Taylor | |
| 5,454,794 A | 10/1995 | Narciso et al. | |
| 5,454,807 A | 10/1995 | Lennox | |
| 5,454,897 A | 10/1995 | Vaniglia | |
| 5,474,564 A | 12/1995 | Clayman et al. | |
| 5,492,122 A | 2/1996 | Button et al. | |
| 5,496,308 A | 3/1996 | Brown et al. | |
| 5,509,917 A | 4/1996 | Cecchetti et al. | |
| 5,530,780 A | 6/1996 | Ohsawa | |
| 5,534,000 A | 7/1996 | Bruce | |
| 5,537,499 A | 7/1996 | Brekke | |
| 5,568,503 A | 10/1996 | Omori | |
| 5,571,099 A | 11/1996 | Purcell, Jr. et al. | |
| 5,620,479 A | 4/1997 | Diederich | |
| 5,632,767 A | 5/1997 | Sinofsky | |
| 5,638,819 A | 6/1997 | Manwaring et al. | |
| 5,672,172 A | 9/1997 | Zupkas | |
| 5,695,501 A | 12/1997 | Carol et al. | |
| 5,719,975 A | 2/1998 | Wolfson et al. | |
| 5,733,277 A | 3/1998 | Pallarito | |
| 5,749,362 A | 5/1998 | Funda et al. | |
| 5,749,549 A | 5/1998 | Ashjaee | |
| 5,752,962 A | 5/1998 | D'Urso | |
| 5,762,066 A | 6/1998 | Law et al. | |
| 5,772,657 A | 6/1998 | Hmelar et al. | |
| 5,785,704 A | 7/1998 | Bille | |
| 5,792,110 A | 8/1998 | Cunningham | |
| 5,807,383 A | 9/1998 | Kolesa et al. | |
| 5,823,941 A | 10/1998 | Shaunnessey | |
| 5,824,005 A | 10/1998 | Motamedi et al. | |
| 5,848,967 A | 12/1998 | Cosman | |
| 5,855,583 A | 1/1999 | Wang et al. | |
| 5,861,020 A | 1/1999 | Schwarzmaier | |
| 5,891,157 A | 4/1999 | Day et al. | |
| 5,947,958 A | 9/1999 | Woodard et al. | |
| 5,949,929 A | 9/1999 | Hamm | |
| 5,959,246 A | 9/1999 | Gretz | |
| 5,978,541 A | 11/1999 | Doiron et al. | |
| 5,989,246 A | 11/1999 | Kaufmann et al. | |
| 5,993,463 A | 11/1999 | Truwit | |
| 6,004,315 A | 12/1999 | Dumont | |
| 6,006,126 A | 12/1999 | Cosman | |
| 6,022,309 A | 2/2000 | Celliers et al. | |
| 6,039,728 A | 3/2000 | Berlien et al. | |
| 6,058,323 A | 5/2000 | Lemelson | |
| 6,071,288 A | 6/2000 | Carol et al. | |
| 6,086,532 A | 7/2000 | Panescu et al. | |
| 6,106,516 A | 8/2000 | Massengill | |
| 6,117,143 A | 9/2000 | Hynes et al. | |
| 6,123,719 A | 9/2000 | Masychev | |
| 6,128,522 A | 10/2000 | Acker et al. | |
| 6,132,437 A | 10/2000 | Omurtag et al. | |
| 6,162,052 A | 12/2000 | Kokubu | |
| 6,164,843 A | 12/2000 | Battocchio | |
| 6,167,295 A | 12/2000 | Cosman | |
| 6,206,873 B1 | 3/2001 | Paolini et al. | |
| 6,206,885 B1 | 3/2001 | Ghahremani et al. | |
| 6,206,890 B1 | 3/2001 | Truwit | |
| 6,246,200 B1 | 6/2001 | Blumenkranz et al. | |
| 6,246,896 B1 | 6/2001 | Dumoulin et al. | |
| 6,254,043 B1 | 7/2001 | Schwärzler | |
| 6,267,769 B1 | 7/2001 | Truwit | |
| 6,267,770 B1 | 7/2001 | Truwit | |
| 6,280,384 B1 | 8/2001 | Loeffler | |
| 6,283,958 B1 | 9/2001 | Vogl et al. | |
| 6,286,795 B1 * | 9/2001 | Johnson | 248/168 |
| 6,293,282 B1 | 9/2001 | Lemelson | |
| 6,332,891 B1 | 12/2001 | Himes | |
| 6,355,028 B2 | 3/2002 | Castaneda et al. | |
| 6,368,329 B1 | 4/2002 | Truwit | |
| 6,368,330 B1 | 4/2002 | Hynes et al. | |
| 6,398,778 B1 | 6/2002 | Gu et al. | |
| 6,413,253 B1 | 7/2002 | Koop | |
| 6,413,263 B1 | 7/2002 | Lobdill et al. | |
| 6,418,337 B1 | 7/2002 | Torchia | |
| 6,423,077 B2 | 7/2002 | Carol et al. | |
| 6,425,867 B1 | 7/2002 | Vaezy et al. | |
| 6,464,690 B1 | 10/2002 | Castaneda et al. | |
| 6,464,691 B1 | 10/2002 | Castaneda et al. | |
| 6,464,694 B1 | 10/2002 | Massengil | |
| 6,491,699 B1 | 12/2002 | Henderson et al. | |
| 6,529,765 B1 | 3/2003 | Franck et al. | |
| 6,544,248 B1 | 4/2003 | Bass | |
| 6,551,274 B2 | 4/2003 | Heiner | |
| 6,558,375 B1 | 5/2003 | Sinofsky et al. | |
| 6,579,281 B2 | 6/2003 | Palmer et al. | |
| 6,589,174 B1 | 7/2003 | Chopra et al. | |
| 6,589,233 B1 | 7/2003 | Maki | |
| 6,695,871 B1 | 2/2004 | Maki et al. | |
| 6,701,181 B2 | 3/2004 | Tang et al. | |
| 6,716,215 B1 | 4/2004 | David et al. | |
| 6,741,883 B2 | 5/2004 | Gildenberg | |
| 6,752,812 B1 | 6/2004 | Truwit | |
| 6,782,288 B2 | 8/2004 | Truwit et al. | |
| 6,843,793 B2 | 1/2005 | Brock et al. | |
| 6,845,193 B2 | 1/2005 | Loeb et al. | |
| 6,893,447 B2 | 5/2005 | Dominguez et al. | |
| 6,902,569 B2 | 6/2005 | Parmer et al. | |
| 6,986,764 B2 | 1/2006 | Davenport et al. | |
| 7,033,367 B2 | 4/2006 | Ghahremani et al. | |
| 7,072,704 B2 | 7/2006 | Bucholz | |
| 7,167,741 B2 | 1/2007 | Torchia et al. | |
| 7,167,760 B2 | 1/2007 | Dawant et al. | |
| 7,235,084 B2 | 6/2007 | Skakoon et al. | |
| 7,235,089 B1 | 6/2007 | McGuckin, Jr. | |
| 7,270,656 B2 | 9/2007 | Gowda et al. | |
| 7,344,529 B2 | 3/2008 | Torchia et al. | |
| 7,366,561 B2 | 4/2008 | Mills et al. | |
| 7,371,210 B2 | 5/2008 | Brock et al. | |
| 7,463,801 B2 | 12/2008 | Brekke et al. | |
| 7,479,139 B2 | 1/2009 | Cytron et al. | |
| 7,736,371 B2 | 6/2010 | Schoepp | |
| 7,794,469 B2 | 9/2010 | Kao et al. | |
| 8,114,068 B2 | 2/2012 | Rheinwald et al. | |
| 8,165,658 B2 | 4/2012 | Waynik et al. | |
| 8,267,938 B2 | 9/2012 | Murphy | |
| 8,285,097 B2 | 10/2012 | Griffin | |
| 8,298,245 B2 | 10/2012 | Li et al. | |
| 8,414,597 B2 | 4/2013 | Kao et al. | |
| 2002/0019641 A1 | 2/2002 | Truwit | |
| 2002/0042605 A1 * | 4/2002 | Castaneda et al. | 606/1 |
| 2002/0052610 A1 * | 5/2002 | Skakoon et al. | 606/129 |
| 2002/0169460 A1 | 11/2002 | Foster et al. | |

(56) References Cited

U.S. PATENT DOCUMENTS

| | | |
|---|---|---|
| 2002/0177843 A1 | 11/2002 | Anderson et al. |
| 2003/0060813 A1 | 3/2003 | Loeb et al. |
| 2003/0171741 A1 | 9/2003 | Ziebol et al. |
| 2004/0075031 A1 | 4/2004 | Crain et al. |
| 2004/0122446 A1 | 6/2004 | Solar |
| 2004/0133190 A1 | 7/2004 | Hobart et al. |
| 2004/0134884 A1 | 7/2004 | Wei et al. |
| 2004/0167542 A1 | 8/2004 | Solar |
| 2004/0167543 A1 | 8/2004 | Mazzocchi et al. |
| 2004/0267284 A1 | 12/2004 | Parmer et al. |
| 2005/0070920 A1 | 3/2005 | Solar et al. |
| 2005/0154378 A1 | 7/2005 | Teague et al. |
| 2006/0009749 A1 | 1/2006 | Weckwerth et al. |
| 2006/0086868 A1* | 4/2006 | White .................. 248/163.1 |
| 2006/0089626 A1 | 4/2006 | Vlegele et al. |
| 2006/0122590 A1 | 6/2006 | Bliweis et al. |
| 2006/0122629 A1 | 6/2006 | Skakoon |
| 2006/0175484 A1 | 8/2006 | Wood, III et al. |
| 2006/0192319 A1 | 8/2006 | Solar et al. |
| 2006/0195119 A1 | 8/2006 | Mazzocchi et al. |
| 2006/0206105 A1 | 9/2006 | Chopra et al. |
| 2006/0212044 A1 | 9/2006 | Bova et al. |
| 2006/0229641 A1 | 10/2006 | Gupta et al. |
| 2006/0287647 A1 | 12/2006 | Torchia et al. |
| 2007/0043342 A1 | 2/2007 | Kleinberger |
| 2007/0100346 A1* | 5/2007 | Wyss et al. .................. 606/87 |
| 2007/0106305 A1 | 5/2007 | Kao et al. |
| 2007/0149977 A1 | 6/2007 | Heavener |
| 2007/0191867 A1 | 8/2007 | Mazzocchi et al. |
| 2007/0208352 A1 | 9/2007 | Henderson et al. |
| 2007/0225562 A1 | 9/2007 | Spivey et al. |
| 2007/0239062 A1 | 10/2007 | Chopra et al. |
| 2007/0250077 A1 | 10/2007 | Skakoon et al. |
| 2007/0270717 A1 | 11/2007 | Tang et al. |
| 2008/0002927 A1 | 1/2008 | Furnish |
| 2008/0027463 A1 | 1/2008 | Labadie et al. |
| 2008/0046122 A1 | 2/2008 | Manzo |
| 2008/0077159 A1 | 3/2008 | Madhani et al. |
| 2008/0097187 A1 | 4/2008 | Gielen et al. |
| 2008/0123921 A1 | 5/2008 | Gielen et al. |
| 2008/0123922 A1 | 5/2008 | Gielen et al. |
| 2008/0195085 A1 | 8/2008 | Loeb |
| 2008/0242978 A1 | 10/2008 | Simon et al. |
| 2008/0243142 A1 | 10/2008 | Gildenberg |
| 2008/0255583 A1 | 10/2008 | Gielen et al. |
| 2008/0269588 A1 | 10/2008 | Csavoy et al. |
| 2008/0269602 A1 | 10/2008 | Csavoy et al. |
| 2008/0287917 A1 | 11/2008 | Cunningham |
| 2008/0306375 A1 | 12/2008 | Sayler et al. |
| 2009/0012509 A1 | 1/2009 | Csavoy et al. |
| 2009/0048588 A1 | 2/2009 | Peng et al. |
| 2009/0112082 A1 | 4/2009 | Piferi et al. |
| 2009/0118610 A1 | 5/2009 | Karmarkar et al. |
| 2009/0124398 A1 | 5/2009 | Thompson |
| 2009/0131783 A1 | 5/2009 | Jenkins et al. |
| 2009/0198309 A1 | 8/2009 | Gowda et al. |
| 2009/0204111 A1 | 8/2009 | Bissig et al. |
| 2009/0240242 A1 | 9/2009 | Neuberger |
| 2009/0287199 A1 | 11/2009 | Hanley et al. |
| 2009/0326525 A1 | 12/2009 | Hixon et al. |
| 2010/0041938 A1 | 2/2010 | Stoianovici et al. |
| 2010/0042112 A1 | 2/2010 | Qureshi et al. |
| 2010/0082035 A1 | 4/2010 | Keefer |
| 2011/0040172 A1 | 2/2011 | Carpentier et al. |
| 2011/0118715 A1 | 5/2011 | Zerfas |
| 2011/0141759 A1 | 6/2011 | Smith |
| 2011/0166447 A1 | 7/2011 | Windolf et al. |
| 2011/0190787 A1 | 8/2011 | Sahni |
| 2011/0217665 A1 | 9/2011 | Walsh et al. |
| 2011/0301450 A1 | 12/2011 | Hue et al. |
| 2011/0319910 A1 | 12/2011 | Roelle et al. |
| 2012/0053573 A1 | 3/2012 | Alksnis |
| 2013/0018430 A1 | 1/2013 | Murphy |
| 2013/0041356 A1 | 2/2013 | Smith et al. |
| 2013/0060253 A1 | 3/2013 | Couture et al. |
| 2013/0085342 A1 | 4/2013 | Stefanchik et al. |

FOREIGN PATENT DOCUMENTS

| | | |
|---|---|---|
| CN | 2748071 Y | 12/2005 |
| CN | 101040772 A | 9/2007 |
| CN | 101194853 A | 6/2008 |
| EP | 0 610 991 A2 | 8/1994 |
| EP | 0 614 651 A1 | 9/1994 |
| EP | 0 755 697 A2 | 1/1997 |
| EP | 1 829 764 | 9/2007 |
| EP | 1 985 330 A1 | 10/2008 |
| JP | 7-308393 | 11/1995 |
| JP | 9-038220 | 2/1997 |
| JP | 10-155805 | 6/1998 |
| JP | 11-253562 | 9/1999 |
| JP | 2000-000319 | 1/2000 |
| JP | 2000-126316 | 5/2000 |
| JP | 2002-543865 | 12/2002 |
| WO | WO 90/05494 | 5/1990 |
| WO | WO 93/20769 | 10/1993 |
| WO | WO 94/04220 | 3/1994 |
| WO | WO 98/51229 | 11/1998 |
| WO | WO 98/52465 | 11/1998 |
| WO | WO 99/51156 | 10/1999 |
| WO | WO 00/23000 | 4/2000 |
| WO | WO 00/67640 | 11/2000 |
| WO | WO 01/76498 A3 | 10/2001 |
| WO | WO 03/094759 A1 | 11/2003 |
| WO | WO 2004/075722 A2 | 9/2004 |
| WO | WO 2005/046451 A2 | 5/2005 |
| WO | WO 2007/056458 A2 | 5/2007 |
| WO | WO 2007-056458 A2 | 5/2007 |
| WO | WO 2007/060474 A1 | 5/2007 |
| WO | WO 2007/064937 | 6/2007 |

OTHER PUBLICATIONS

Office Action mailed Dec. 27, 2013, in Israeli Patent Application No. 210878.

Office Action mailed Oct. 8, 2012, in Chinese Patent Application No. 200980131600.9 (with English-language translation).

International Search Report and Written Opinion mailed Jun. 10, 2013, in PCT/US13/32273.

International Preliminary Report on Patentability mailed Feb. 15, 2011, in PCT/CA2009/001138, 5 pages.

Office Action mailed Oct. 25, 2011, in Brazilian Patent Application No. PI-0214951-6 (English translation).

Office Action mailed May 28, 2013, in Brazilian Patent Application No. PI-0214951-6 (English translation).

Office Action mailed Nov. 1, 2012, in Japanese Patent Application No. 2011-522361 (with English-language translation).

Combined Chinese OA and Search Report mailed Mar. 13, 2013, in Chinese Patent Application No. 200980131609.X.

Office Action mailed Aug. 22, 2013, in Chinese Patent Application No. 200980131600.9 (with English-language translation).

Kahn et al., "MRI-Guided Laser-Induced Interstitial Thermotherapy of Cerebral Neoplasms," Journal of Computer Assisted Tomography, vol. 18, No. 4, pp. 519-532, Jul./Aug. 1994, Raven Press, Ltd., New York, NY.

Kahn et al., "In Vivo MRI Thermometry Using a Phase-Sensitive Sequence: Preliminary Experience During MRI-Guided Laser-Induced Interstitial Thermotherapy of Brain Tumors," Journal of Magnetic Resonance Imaging, vol. 8, No. 1, pp. 160-164, Williams & Wilkins, 1998, Baltimore, MD.

Vogl et al., "Internally Cooled Power Laser for MR-guided Interstitial Laser-induced Thermotherapy of Liver Lesions: Initial Clinical Results", in Radiology, 1998, 209: pp. 381-385.

(56) References Cited

OTHER PUBLICATIONS

McNichols et al., "MR Thermometry-Based Feedback Control of Laser Interstitial Thermal Therapy at 980 nm," Lasers in Surgery and Medicine, 2004, 34: 48-55, Wiley-Liss, Inc.

Schwarzmaier et al., "MR-guided laser-induced interstitial thermotherapy of recurrent glioblastoma multiforme: Preliminary results in 16 patients," European Journal of Radiology, vol. 59, Issue 2, pp. 208-215, Aug. 2006.

Office Action mailed Jul. 17, 2013, in Japanese Patent Application No. 2011-522361 (with English-language translation).

Office Action mailed Jul. 29, 2013, in Japanese Patent Application No. 2011-522360 (with English-language translation).

Office Action issued in Chinese Patent Application No. 200980131609.X on Jan. 10, 2014.

Office Action issued in U.S. Appl. No. 13/932,725 on Feb. 28, 2014.

\* cited by examiner

TRAJECTORY GUIDE

CROSS-REFERENCE TO RELATED APPLICATION(S)

This application claims the benefit of U.S. Provisional Application Ser. No. 61/089,224, filed Aug. 15, 2008, and U.S. Provisional Application Ser. No. 61/170,859, filed Apr. 20, 2009, the entireties of which are hereby incorporated by reference.

FIELD OF THE INVENTION

The present invention is related to surgical working platforms. More specifically, the present invention relates to a trajectory guide and method for using the same which facilitates the alignment of surgical and observational instruments into a patient.

BACKGROUND OF THE INVENTION

Each year roughly 200,000 patients are diagnosed with brain tumors in the United States. Roughly 17,000 of these tumors are "benign," meaning that the tumor mass is not cancerous. However, the other roughly 183,000 of these tumors are "malignant" (i.e., cancerous), meaning that they are capable of causing or contributing to patient death. Approximately 10% of cancerous brain tumors are "primary" tumors, meaning that the tumors originate in the brain. The primary tumors typically consist of brain tissue with mutated DNA that aggressively grows and displaces or replaces normal brain tissue. The most common of the primary tumors are known as gliomas, which indicate cancer of the glial cells of the brain. In most instances, primary tumors appear as single masses. However, these single masses can often be quite large, irregularly-shaped, multi-lobed and/or infiltrated into surrounding brain tissue.

Primary tumors are generally not diagnosed until the patient experiences symptoms, such as headaches, altered behavior, sensory impairment, or the like. However, by the time the symptoms develop the tumor may already be large and aggressive.

Various treatments for brain tumors exist and several involve accessing the brain so that treatment of the tumor can be effected. One such method of treatment involves the treatment of tumors by "heat" (also referred to as hyperthermia or thermal therapy). In particular, it is known that above 57 C all living tissue is almost immediately and irreparably damaged and killed through a process called coagulation necrosis or ablation. Malignant tumors, because of their high vascularization and altered DNA, are more susceptible to heat-induced damage than normal tissue. Various types of energy sources may be used, such as laser, microwave, radiofrequency, electric, and ultrasound sources. Depending upon the application and the technology, the heat source may be extracorporeal (i.e. outside the body), extrastitial (i.e. outside the tumor), or interstitial (i.e. inside the tumor).

Interstitial thermal therapy (ITT) is a process designed to heat and destroy a tumor from within the tumor. One advantage of this type of therapy is that the energy is applied directly to the tumor rather than passing through surrounding normal tissue. Another advantage of the type of therapy is that the energy deposition is more likely to be extended throughout the entire tumor.

One exemplary ITT process involves the use of laser (LITT) and begins by inserting an optical fiber into the tumor, wherein the tumor has an element at its "inserted" end that redirects laser light from an exterior source in a direction generally at right angles to the length of the fiber. The energy from the laser thus extends into the tissue surrounding the end or tip and effects heating. The energy is directed in a beam confined to a relatively shallow angle so that, as the fiber is rotated, the beam also rotates around the axis of the fiber to effect heating of different parts of the lesion at positions around the fiber. The fiber can thus be moved longitudinally and rotated to effect heating of the lesion over the full volume of the lesion with the intention of heating the lesion to the required temperature without significantly affecting tissue surrounding the lesion.

To locate the tumor or other lesion to be treated with LITT, magnetic resonance imaging is frequently used. Although these imaging systems have been helpful to assist the surgeon in determining a location of the lesion to be treated, an instrument for determining the trajectory for entry of the optical fiber into the brain is necessary in order to ensure controlled accuracy in treating the tumor. Several conventional methods and apparatuses are used to determine trajectory so that surgical and observational instruments may be inserted in the patient's brain.

Stereotactic neurosurgery is a field of neurosurgery in which a probe is advanced through a burr hole to a target of interest by means of a mechanical device attached to the skull with aiming based on pre-operative images. The probe may be a biopsy needle or an implantable device, but it is geometrically rigid, so that its tip can be brought to a target of interest specified on a pre-operative image, by means of a geometrical calculation. For the past decade, the field has been advancing from the imposition of large, classical metal frames, which encompass the entire head of a patient, to the attachment of small platforms placed only over an entry site to reduce patient discomfort, facilitate surgical access, allow multiple targeting during one surgery via multiple platforms, and reduce procedure time, while maintaining the same level of accuracy.

Classical metal frames are designed for approaching one target at a time with an unrestricted entry point towards the deep target by employing the principle that the target is at the center of a sphere. Because of the long trajectories, both accuracy and patient comfort are challenged by the demands of surgeries for deep brain stimulation (DBS) in which the patients are awake throughout the lengthy surgery procedure (about 5-8 hours).

During the last few years, microplatforms have become available as replacements for the classical frames for DBS stereotactic surgery.

U.S. Pat. No. 6,206,890 to Truwit discloses an apparatus for aligning the trajectory of, guiding, and introducing and withdrawing a surgical probe to treat a brain tumor. The apparatus includes a unitary base which has a ball joint member that is movably attached to the base. The ball joint member has a passage therein which forms a portion of the trajectory path. The ball joint member also includes a long, cylindrical, thin-walled guide stem which has an opening therein that substantially aligns with the passage in the moveable member. The ball joint member includes either an integral guide stem for holding the positioning stem or a removably attached guide stem. In the case of the former, a positioning stem is inserted into the opening of the guide stem for purposes of trajectory alignment. In the case of the latter, the removably attached guide stem can be removed and replaced with a positioning stem.

However, there are problems regarding geometric stability, limited space for access to the burr hole and surgical manipulation once the tower is mounted, the time consuming process of aiming, and the difficulty of locking on the target. Access to the burr hole is crucially important for the purpose of stopping bleeding from the bone cavity, dura, and the surface of the cortex during the procedure. Aiming is achieved by watching a guiding icon on the screen of the intraoperative tracking system, while adjusting the orientation of the platform. When the icon indicates a correct trajectory, the platform must be locked into place with one hand, while it is held at the correct trajectory with the other. The trajectory is two-dimensional, meaning that there are two mutually perpendicular angular adjustments required, each of which must be set simultaneously for the correct trajectory. Finding the correct trajectory via the guiding icon is time consuming because of the difficulty of making fine adjustments of one angle of the approach without changing the other angle. A further difficulty with this aiming procedure is maintaining both angles of the correct trajectory while locking the device on target. The locking step can be especially frustrating, because, if either angle is changed inadvertently during locking, as revealed by the guiding icon, the device must be unlocked and the adjustment started from the beginning. Typically several iterations are required, resulting in wasted operating time.

U.S. Pat. No. 7,167,760 to Dawant et al. discloses a device that also requires the attachment of bone-implanted fiducials and the subsequent acquisition of a preoperative tomogram, but it does not require intraoperative optical tracking for aiming. Instead the device is custom made for each patient based on a pre-operative tomogram and the surgeon's identification of the entry point and the target on that tomogram. Thus, the device arrives at the operating suite pre-aimed with no adjustment required intraoperatively. It is a one-piece rigid plastic block having a cylindrical hole that accommodates the probe, supported by a plurality of legs, each of which attaches to a base that is implanted in the skull. Fiducial markers are attached to these same bases before the pre-operative image is acquired and discarded after imaging. The shape of the device provides far greater access to the burr hole but does not allow the surgeon total flexibility in changing trajectory. In addition, while the device is disposable a significant disadvantage is that the patient must wait between the acquisition of the tomogram and the delivery of the device which can range from two to four days.

U.S. Patent Publn. 2007/0106305 attempts to address the shortcomings of the Dawant device by disclosing a surgical platform that includes a ring structure and a ball joint that is configured to be received in the ring structure, where the ball joint defines a bore for accommodating a surgical probe therethrough. The surgical platform includes a plurality of threadably-adjustable leg assemblies. While the adjustable legs provide the surgeon with the ability to make macro and micro adjustments, mechanically the device is cumbersome to use.

Therefore, a heretofore unaddressed need exists to establish a rigid, secure apparatus for holding a long cylindrical medical device in a fixed, three-dimensional trajectory relative to the patient, that is able to withstand torquing, bumping and other potentially dislodging or disorienting forces during patient transfer from the operating room to the MRI suite and while in the MRI suite during the procedure. A further need exists that will give the surgeon complete maneuverability to easily and quickly make macro changes or fine adjustments to the trajectory; to change the position of the medical device when desired and as needed in the MRI; and to visualize the surgical site. The device must be MRI-compatible, lightweight and able to be easily affixed to the patient. The maneuverability allows the surgeon to drill multiple holes.

BRIEF SUMMARY OF THE INVENTION

These and other advantages are accomplished by the trajectory guide in accordance with the present invention. The present invention relates to an MRI-compatible trajectory guide for providing access to a target site of a living subject along a desired path. In one embodiment, the trajectory guide includes a baseplate including a clamp lock, a guide member at least partially contained within the baseplate and having a channel therein, a plurality of adjustable legs each including a first end and a second end, wherein the first end is coupled to the baseplate, and a leg lock coupled to each adjustable leg and moveable between an unlocked position and a locked position in order to set a desired length of the adjustable leg, wherein the adjustable legs and the guide member are structured to be adjusted to provide an infinite number of trajectories in three-dimensional space extending through the channel in the guide member toward a target.

DETAILED DESCRIPTION OF THE INVENTION

Generally speaking, the present invention encompasses a trajectory guide structured to provide a strong and rigid platform for applications such as neurosurgery which require trajectory alignment. When unlocked, the trajectory guide may be manipulated to align with a wide range of trajectories. In one exemplary embodiment, a plurality of adjustable legs and an adjustable guide member of the trajectory guide may be structured to provide an infinite number of trajectories in three-dimensional space extending through a channel in the guide member toward a target. When locked, the device may provide a secure and rigid interface for a variety of neurosurgical applications. Examples of these applications include, but are not limited to, laser treatment, biopsy, catheter placement, drug delivery, deep brain stimulation, drain hole creation such as for ventriculostomies, and burr hole creation. As will be appreciated by those skilled in the art, the trajectory guide may be useful for applications other than neurosurgical applications without departing from the intended scope of the present invention.

Figure 1:
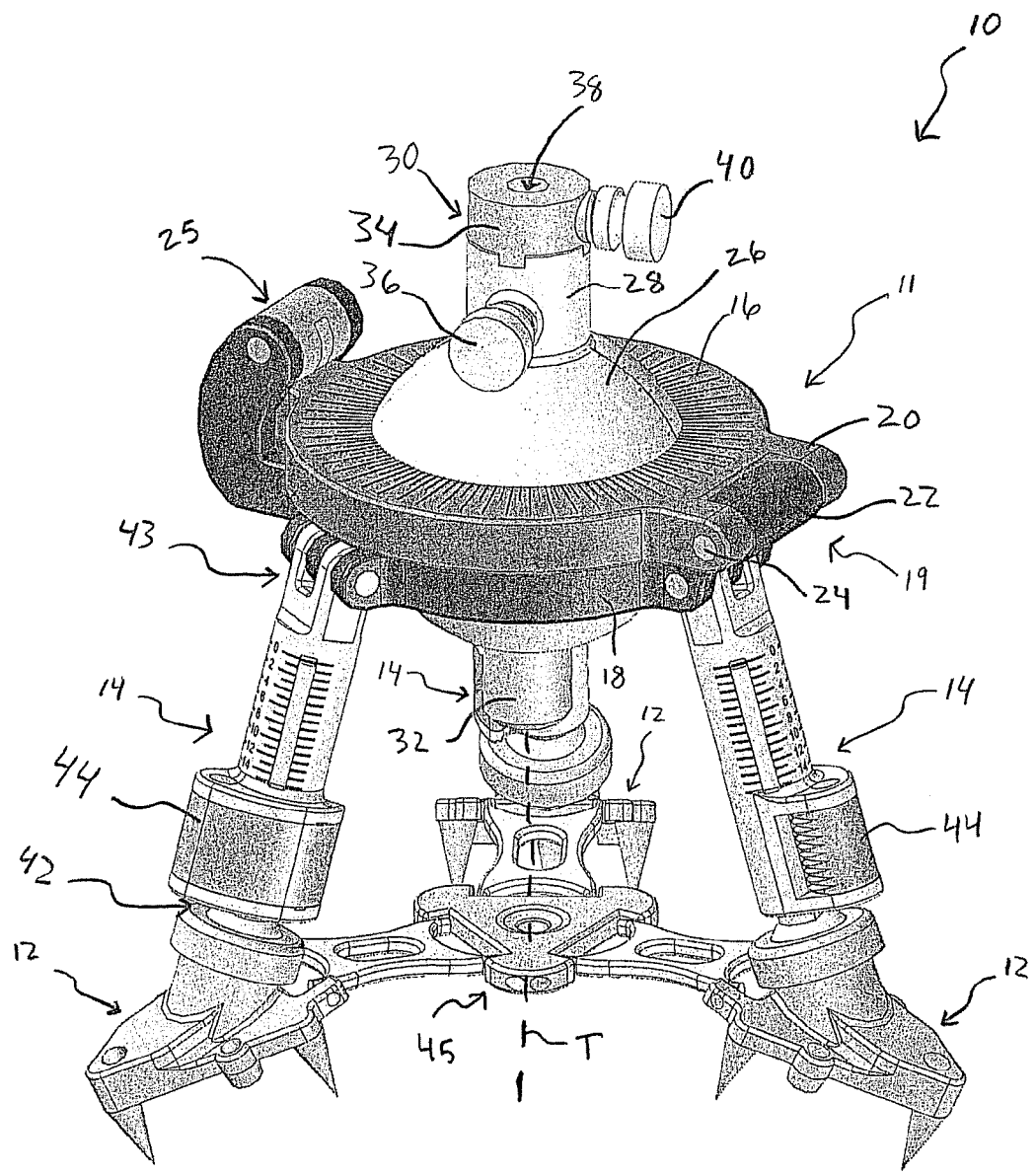
FIG. 1 is a perspective view of a trajectory guide in accordance with one exemplary embodiment of the present invention.

FIG. 1 is a perspective view one exemplary embodiment of a trajectory guide 10 in accordance with the present invention, which generally includes a base plate 11, a plurality of feet 12 attachable to the skull or other body part of a patient, and a plurality of adjustable, telescoping legs 14 equal in number to the plurality of feet 12. As illustrated in FIG. 1, the trajectory guide 10 may be oriented to define a trajectory line T for tools or instruments that require alignment. Tools or instruments may include, but are not limited to, probes, catheters, biopsy needles, drills, and the like.

The base plate 11 of the trajectory guide 10 includes a top clamp 16, which includes a first disk having a first hole, and a bottom clamp 18, which includes a second disk having a second hole, hingedly coupled together by hinge means 19, which may include a first hinge portion 20 extending from the top clamp 16 that is structured to mate with a second hinge portion 22 extending from the bottom clamp 18. The first and second hinge portions 20 and 22 may be coupled together via any suitable connection means, such as a pin 24 or similar connection device. Furthermore, the top clamp 16 and the bottom clamp 18 may be locked together in a closed position with a clamp lock 25 after the trajectory is determined.

The top and bottom clamps 16 and 18 each include an opening that is structured to allow a ball joint moveable member 26 to be moveably and rotatably seated therebetween. The ball joint moveable member 26 may include an adapter receiving member 28 and a central receiving lumen (not shown in FIG. 1) extending through the adapter receiving member 28 and the ball joint moveable member 26. The adapter receiving member 28 of the ball joint moveable member 26 may be structured to receive a center ball adapter 30 therein that may in turn be structured to receive and interface with various tools.

As illustrated in FIG. 1, the center ball adapter 30 passes through the ball joint moveable member 26 from the top and includes a tubular portion 32 and an interface portion 34 structured to mate with the adapter receiving member 28 of the ball joint moveable member 26. A first fastening means 36 may be coupled to the adapter receiving member 28 that is operable to secure the center ball adapter 30 to the ball joint moveable member 26 after it has been inserted therethrough. Particularly, the first fastening means 36 may be any suitable fastening means including, but not limited to, a thumb screw or the like. After fully inserting the center ball adapter 30 into the adapter receiving member 28 of the ball joint moveable member 26, the thumb screw may be tightened to lock it in place. Thereafter, the user may remove the center ball adapter 30 by simply loosening the thumb screw and sliding the adapter 30 from within the adapter receiving member 28.

The center ball adapter 30 may include a lumen 38 extending through the tubular portion 32 and the interface portion 34 that is structured to receive a surgical tool. The diameter of the lumens in various center ball adapters may vary depending upon the size of the probe and/or instrument that the lumen is designed and structured to receive. Additionally, the center ball adapter 30 may include a second fastening means 40 that is operable to secure the tool in place once it has been positioned within the lumen 38. As will be appreciated by those skilled in the art, the second fastening means 40 may be similar to the first fastening means 36 previously described.

As illustrated in FIG. 1, each of the adjustable, telescoping legs 14 may include a ball joint end 42 and a hinged end 43. As will be discussed in further detail to follow, a length of each leg 14 may be adjusted and the leg locked at a desired length with a leg cam lock 44 after the trajectory is determined.

As further illustrated in FIG. 1, the trajectory guide 10 may optionally include a web assembly 45 designed to assist with the proper spacing and alignment of the feet 12 during the placement of the trajectory guide 10 on the patient. However, it will be obvious to those skilled in the art that the web assembly 45 is not a necessary component of the present invention and the trajectory guide 10 may be placed on the patient without the use of such device.

Figure 2A:
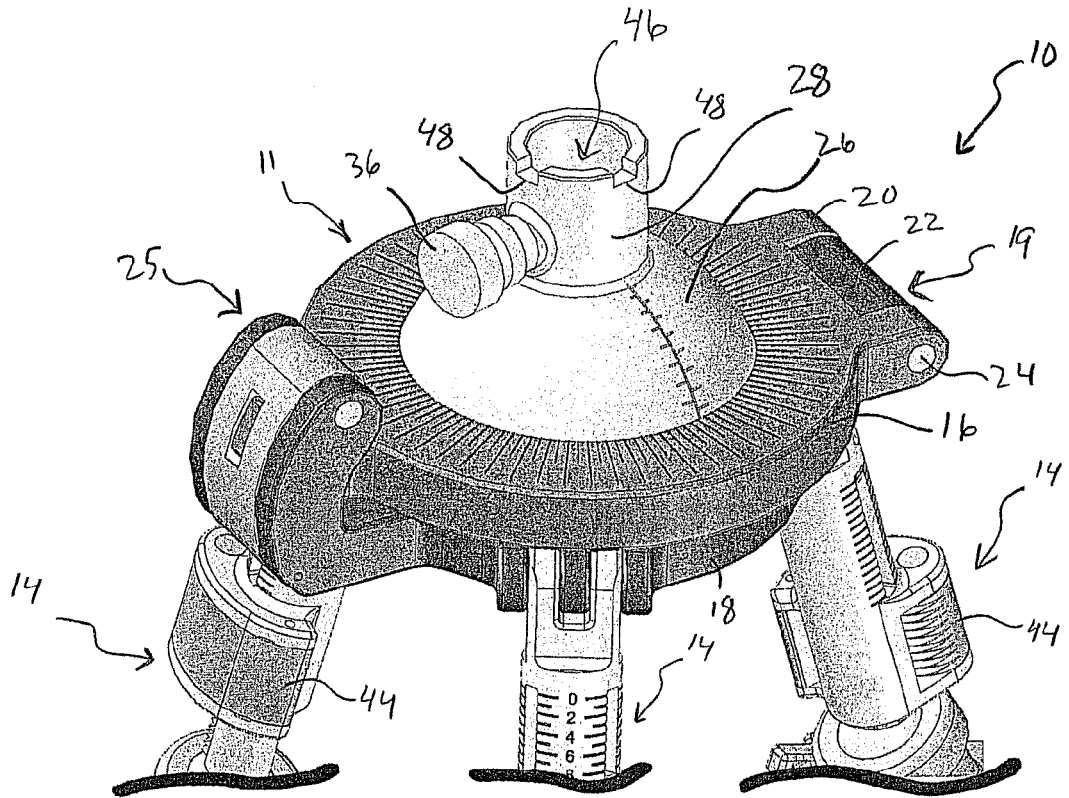
FIG. 2A is an enlarged perspective view of the trajectory guide of FIG. 1 illustrating an interface means of an adapter receiving member.
Figure 2B:
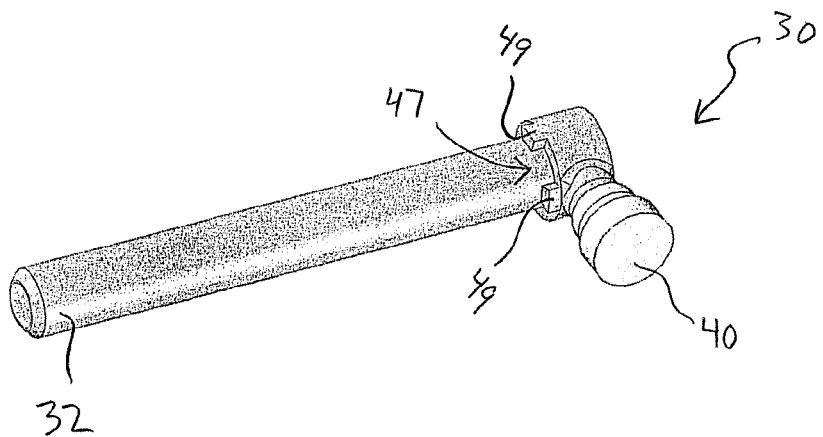
FIG. 2B is a perspective view of a center ball adapter illustrating an interface means thereof.

FIG. 2A is an enlarged perspective view of the trajectory guide 10 illustrating an interface means 46 of the adapter receiving member 28, while FIG. 2B is a perspective view of the center ball adapter 30 illustrating an interface means 47 thereof. In the exemplary embodiment illustrated in FIGS. 2A and 2B, the interface means 46 comprises a pair of notches 48 in the adapter receiving member 28, while the interface means 47 comprises a corresponding pair of tabs 49 structured to mate with the pair of notches 48. As will be appreciated by those skilled in the art, the interface means 46 and 47 function such that the center ball adapter 30 may only be inserted into the adapter receiving member 28 in one specific orientation. This directional interface allows for "indexing" the tools positioned within the center ball adapter 30 relative to the ball joint moveable member 26.

As will be appreciated by those skilled in the art, interface means that comprise a pair of notches and a corresponding pair of tabs are merely one example of an interface means in accordance with the present invention. In one alternative embodiment, a single tab and notch may be utilized. In another alternative embodiment, more than two corresponding tabs and notches may be utilized. In yet another alternative embodiment, the position of the notches and the tabs may be reversed such that the notches are positioned within the center ball adapter 30 and the tabs are positioned on the adapter receiving member 28. Various types of interface means other than notches structured to receive mating tabs are also contemplated and within the intended scope of the present invention.

Figure 3A:
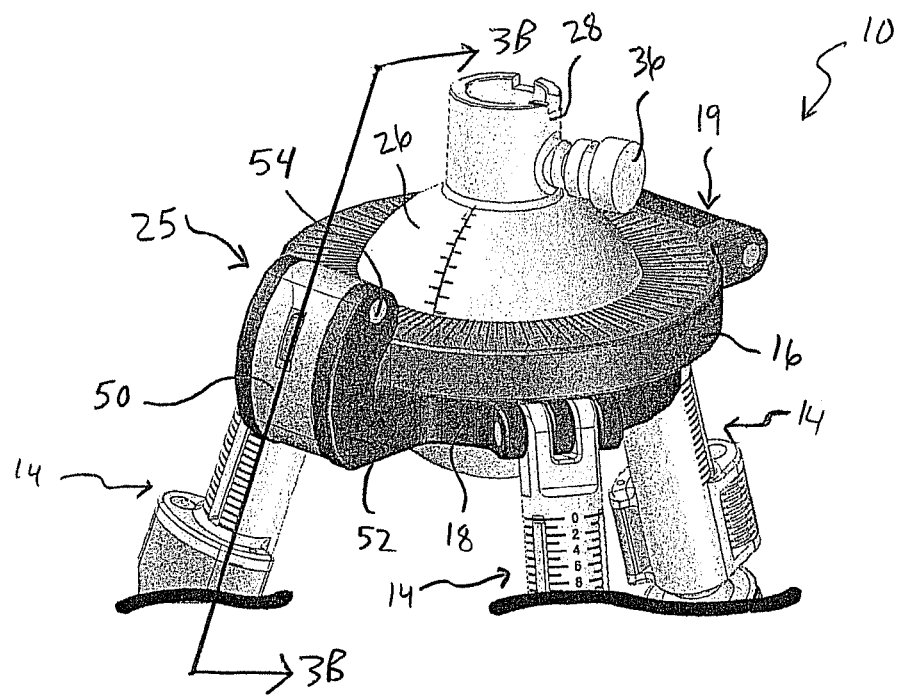
FIG. 3A is a perspective view of a portion of the trajectory guide of FIG. 1 illustrating a clamp lock in a closed and locked position.
Figure 3B:
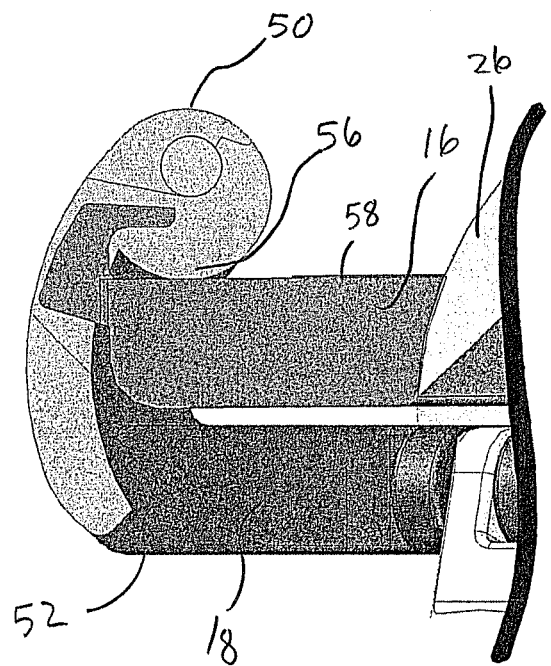
FIG. 3B is a cross-sectional view of a portion of the trajectory guide taken along line 3B-3B of FIG. 3A.

FIG. 3A is a perspective view of a portion of the trajectory guide 10 in accordance with the present invention illustrating the clamp lock 25 in a closed and locked position, while FIG. 3B is a cross-sectional view of a portion of the trajectory guide 10 taken along line 3B-3B of FIG. 3A. As illustrated in FIGS. 3A and 3B, the clamp cam lock 25 includes a cam lever 50 coupled to a lock base 52 extending from the bottom clamp 18. The cam lever 50 may be coupled to the lock base 52 via any suitable connection means. For example, as illustrated in FIG. 3A, the cam lever 50 is hingedly coupled to the lock base 52 with a hinge pin 54. When the clamp lock 25 is in the locked position as illustrated in FIGS. 3A and 3B, a curved portion 56 of the cam lever 50 is structured to apply pressure to a top surface 58 of the top clamp 16, which in turn applies pressure to the ball joint moveable member 26 which is clamped between the top clamp 16 and the bottom clamp 18. Stated alternatively, closing the clamp lock 25 as illustrated in FIGS. 3A and 3B "squeezes" the ball joint moveable member 26 between the top clamp 16 and the bottom clamp 18. As a result, the ball joint moveable member 26 becomes locked and cannot rotate relative to the base plate 11.

Figure 4A:
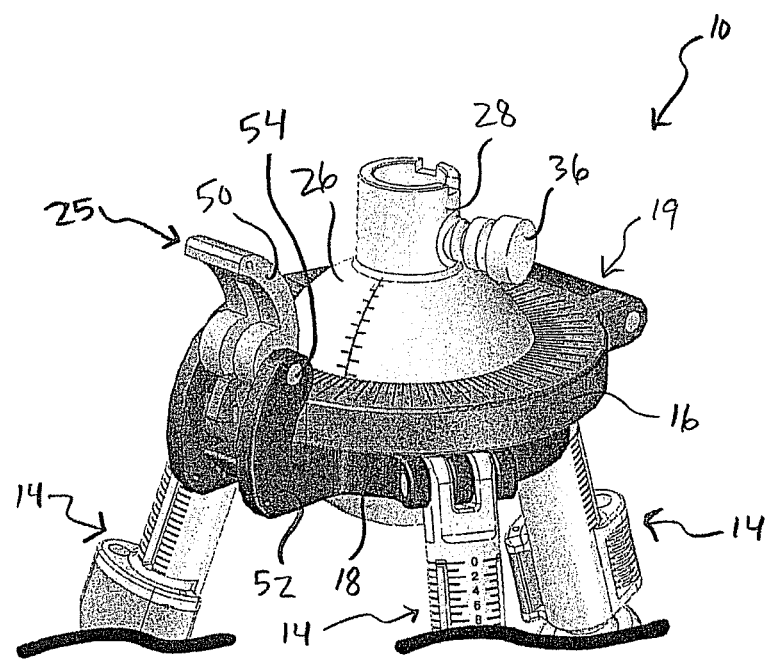
FIG. 4A is a perspective view of a portion of the trajectory guide of FIG. 1 illustrating the clamp lock in an open and unlocked position.
Figure 4B:
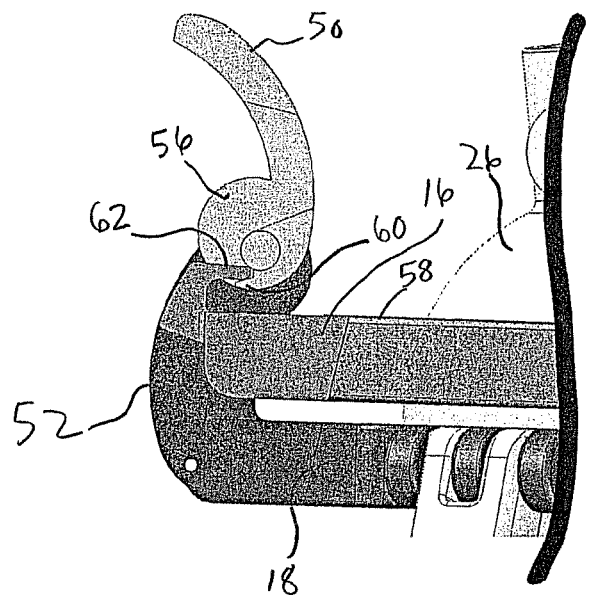
FIG. 4B is a cross-sectional view of the portion of the trajectory guide shown in FIG. 4A.

In order to adjust the position of the ball joint moveable member 26, and thus the trajectory line of the trajectory guide 10, the surgeon simply rotates the cam lever 50 relative to the lock base 52 to the unlocked position as illustrated in FIGS. 4A and 4B. Particularly, FIGS. 4A and 4B represent views of the trajectory guide 10 similar to those illustrated in FIGS. 3A and 3B, but instead depict the clamp lock 25 in the open, unlocked position. As best illustrated in FIG. 4B, when the clamp lock 25 is fully opened, a hook portion 60 of the cam lever 50 engages with and hooks onto a flange member 62 extending from the top clamp 16, thereby lifting the top clamp 16 slightly. The action of lifting the top clamp 16 releases the center ball joint moveable member 26 and allows the ball joint moveable member 26 to be rotated relative to the base plate 11 without grabbing onto either the top clamp 16 or the bottom clamp 18.

Figure 5A:
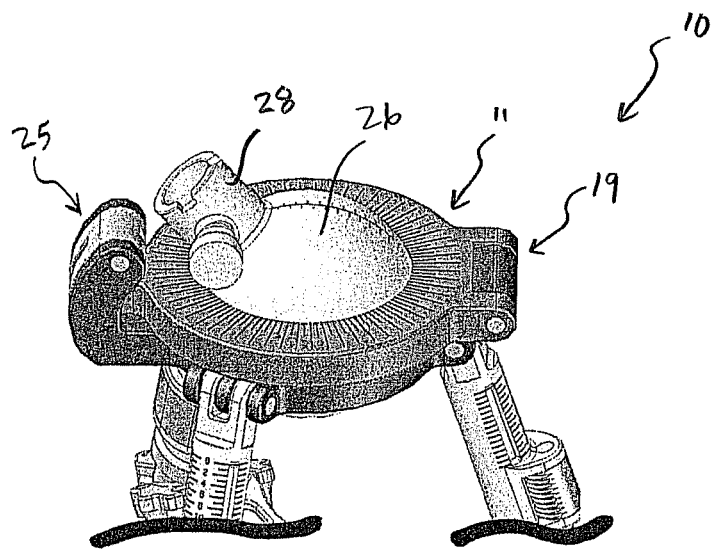
FIGS. 5A and 5B illustrate an exemplary range of motion of a ball joint moveable member of the trajectory guide.
Figure 5B:
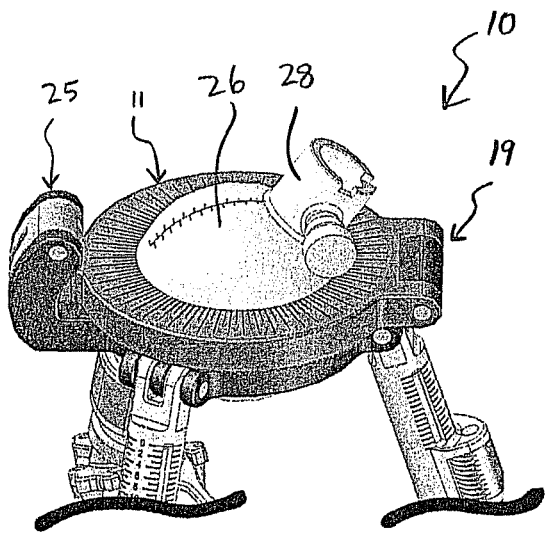

An exemplary range of motion of the ball joint moveable member 26 is shown in FIGS. 5A and 5B. Particularly, FIG. 5A illustrates the ball joint moveable member 26 in a first position such that the adapter receiving member 28 is positioned adjacent the clamp lock 25. In order to adjust the position of the ball joint moveable member 26, the clamp lock 25 may be moved to the unlocked position as illustrated in FIGS. 4A and 4B to allow the ball joint moveable member 26 to rotate and move freely within the baseplate 11, between the top clamp 16 and the bottom clamp 18. FIG. 5B illustrates the ball joint moveable member 26 after being rotated to a second position and locked in place as discussed above with reference to FIGS. 3A and 3B such the adapter receiving member 28 is now positioned adjacent the hinge means 19. The range of motion illustrated in FIGS. 5A and 5B is presented merely for purposes of example and not limitation. Because the ball joint moveable member 26 has a generally spherical shape, it provides a pivot point, may be rotated to any number of positions and is only limited in movement by contact between the adapter receiving member 28 and the top clamp 16.

Figure 6:
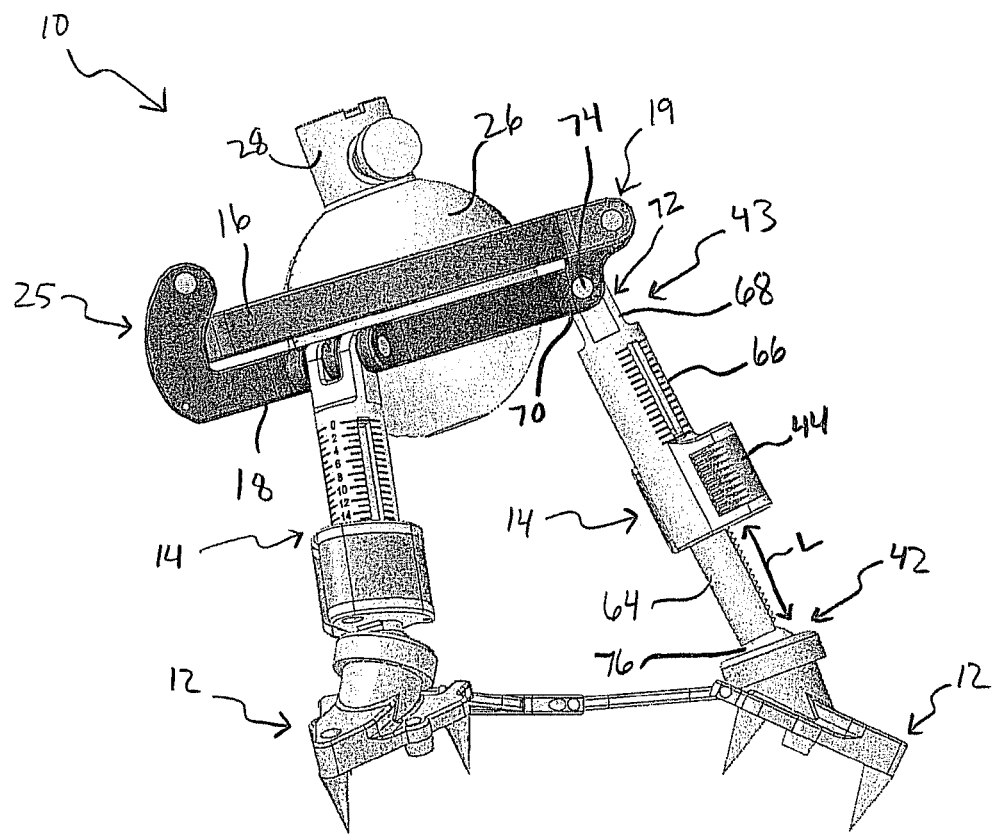
FIG. 6 is a side view of the trajectory guide with a telescoping leg of the trajectory guide in an extended position.

In addition to adjusting the trajectory line of the trajectory guide 10 by rotating the ball joint moveable member 26 with respect to the base plate 11, the trajectory line of the trajectory guide 10 may also be adjusted by changing the length of one or more of the telescoping legs 14 supporting the base plate 11. Particularly, changing the length of each leg alters the angle of the bottom clamp 18, which in turn alters the trajectory of the ball joint moveable member 26. FIG. 6 is a side view of the trajectory guide 10 with one of the telescoping legs 14 in an extended position. Particularly, each telescoping leg 14 includes an inner portion 64 slidingly received into an outer portion 66 producing a linear length of travel L. As illustrated in FIG. 6, the outer portion 66 includes the hinged end 43 while the inner portion 64 includes the ball joint end 42. However, the positions of the inner and outer portions 64 and 66 may be reversed such that the outer portion 66 includes the ball joint end 42 and the inner portion 64 includes the hinged end 43 without departing from the intended scope of the present invention.

The hinged end 43 of the outer portion 66 of the telescoping leg 14 may include a first hinge portion 68 that is structured to be received by a second hinge portion 70 extending from the bottom clamp 18 of the base plate 11, thereby forming a hinge means 72. As illustrated in FIG. 6, the hinge means 72 may include a pin member 74 for coupling the first hinge portion 68 to the second hinge portion 70. The hinge means 72 may be designed as a "triple hinge joint" that is structured to eliminate or reduce the "play" between the bottom clamp 18 and the telescoping leg 14. Minimizing the clearances between the first hinge portion 68, the second hinge portion 70, and the pin member 74 may further reduce or eliminate unwanted movement between the telescoping legs 14 and the bottom clamp 18.

The ball joint end 42 of the inner portion 64 of each telescoping leg 14 includes a ball joint 76 that is structured to be received by a socket in the corresponding foot 12. As will be appreciated by those skilled in the art, the ball joint 76 provides the trajectory guide 10 with a full range of angular travel so that the position of each of the telescoping legs 14 may be set independently.

In one exemplary embodiment, each telescoping leg 14 may have a linear travel of about 15 mm, which provides an angular range of motion of approximately 32° (at the baseplate 11). However, telescoping legs may be designed having any suitable amount of linear travel without departing from the intended scope of the present invention. For instance, the amount of linear travel that is necessary may depend upon the size of the trajectory guide or the range of movement of the ball joint moveable member.

Figure 7A:
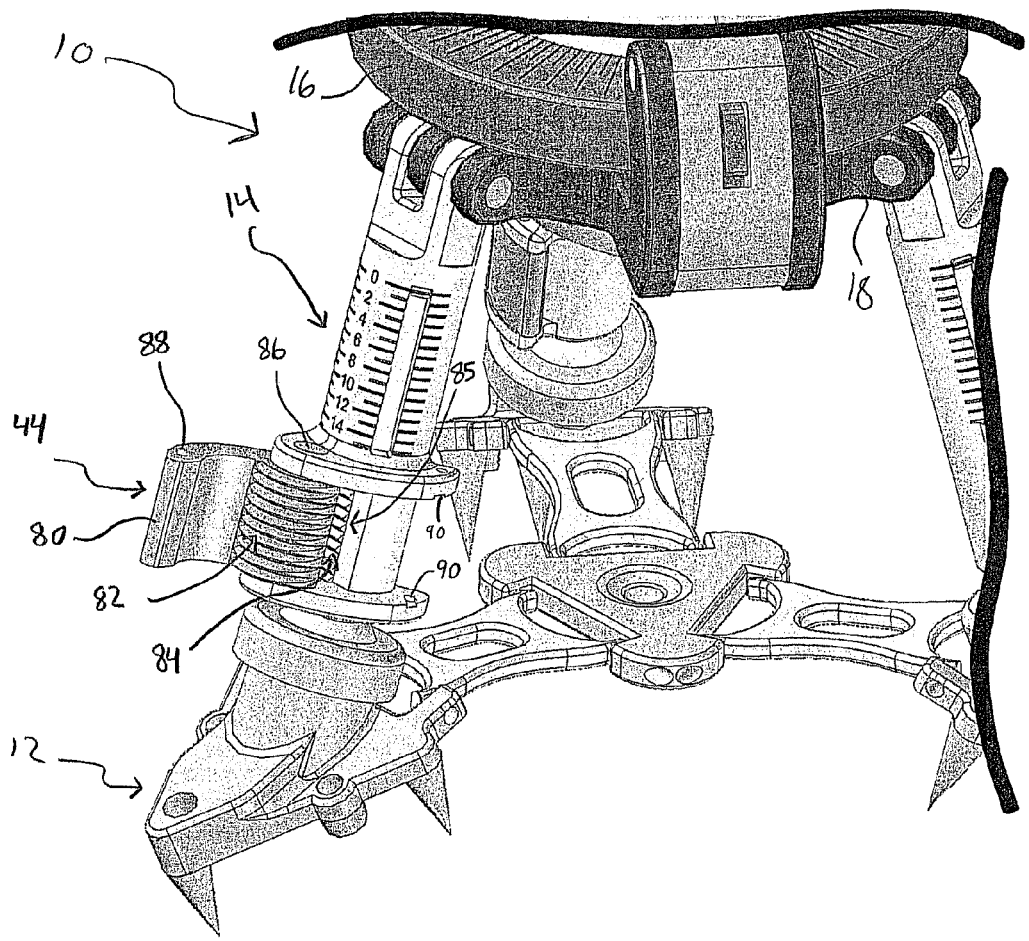
FIG. 7A is a perspective view of a portion of the trajectory guide illustrating the operation of a leg lock.

As discussed above, once the inner portion 64 of the telescoping leg 14 has been adjusted relative to the outer portion 66 such that a desired leg length has been obtained, the telescoping leg 14 may be locked with the leg cam lock 44. FIG. 7A is a perspective view of a portion of the trajectory guide 10 illustrating the leg cam lock 44 in an open and unlocked position. In one exemplary embodiment, the leg lock 44 may be similar in operation to the clamp lock 25 used to lock the ball joint moveable member 26 between the top and bottom clamps 16 and 18 of the baseplate 11. As will be appreciated by those skilled in the art, when the leg lock 44 is in the open and unlocked position as illustrated in FIG. 7A, the leg 14 is allowed to telescope freely as previously discussed with respect to FIG. 6 in order to adjust a length of the leg. However, when the leg cam lock 44 is closed and in the locked position, the inner and outer portions 64 and 66 of the telescoping leg 14 are locked in place in order to set the desired length of the leg.

As illustrated in FIG. 7A, the leg lock 44 includes a cam lever 80 and a set of teeth 82 that are structured to engage a corresponding set of teeth 84 on the inner portion 64 of the telescoping leg 14 (which are best shown in FIG. 6) when the cam lever 80 is rotated to the locked position. The teeth 84 on the inner portion 64 of the telescoping leg 14 are exposed through an opening 85 in the outer leg portion 66. In one exemplary embodiment, the two sets of teeth 82 and 84 may each have a pitch of about 1 mm, although any suitable pitch may be utilized as will be obvious to those skilled in the art.

In order to move between the locked and unlocked position, the cam lever 80 may be hingedly coupled to the outer leg portion 66 via any suitable hinge member, such as a pair of post members 86 (only one being shown) structured to be received by apertures within the outer portion 66. Additionally, one or more dimples 88 or similar structures on the cam lever 80 of the leg lock 44 that are structured to be received by corresponding wells 90 in the outer portion 66 may be utilized in order to maintain the leg lock 44 in the closed and locked position (as illustrated in FIG. 6).

Figure 7B:
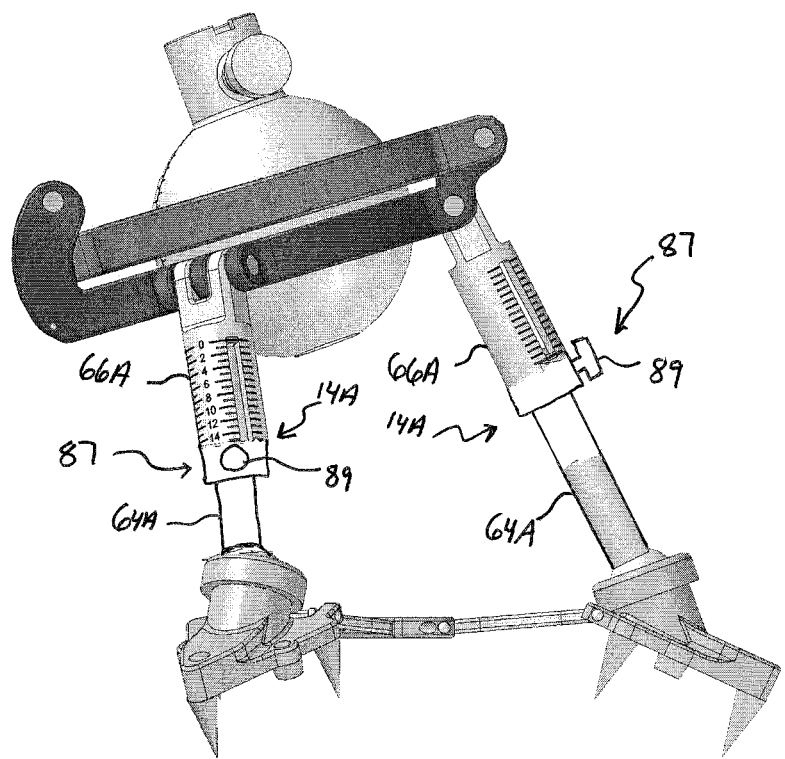
FIG. 7B is a perspective view of the trajectory guide illustrating an alternative leg lock in accordance with the present invention.

As will be appreciated by those skilled in the art, the leg lock 44 having a cam lever 80 and a set of teeth 82 that engages with a corresponding set of teeth 84 on the leg represents merely one type of leg locking means that may be utilized in accordance with the trajectory guide of the present invention. One exemplary alternative embodiment of a leg lock 87 is illustrated in FIG. 7B. As shown in FIG. 7B, leg lock 87 may generally include a fastening means 89 that is insertable through the outer leg portion 66A and structured to engage the inner leg portion 64A in order to set the length of the telescoping leg 14A. The fastening means 89 may be any suitable fastening means including, but not limited to, a thumb screw or the like. For example, upon sliding the inner leg portion 64A with respect to the outer leg portion 66A to obtain the desired length of the telescoping leg 14A, the thumb screw may be tightened to lock the positions of the leg portions. Thereafter, the user may adjust the length of the leg 14A by simply loosening the thumb screw as will be appreciated by those skilled in the art.

Figure 8:
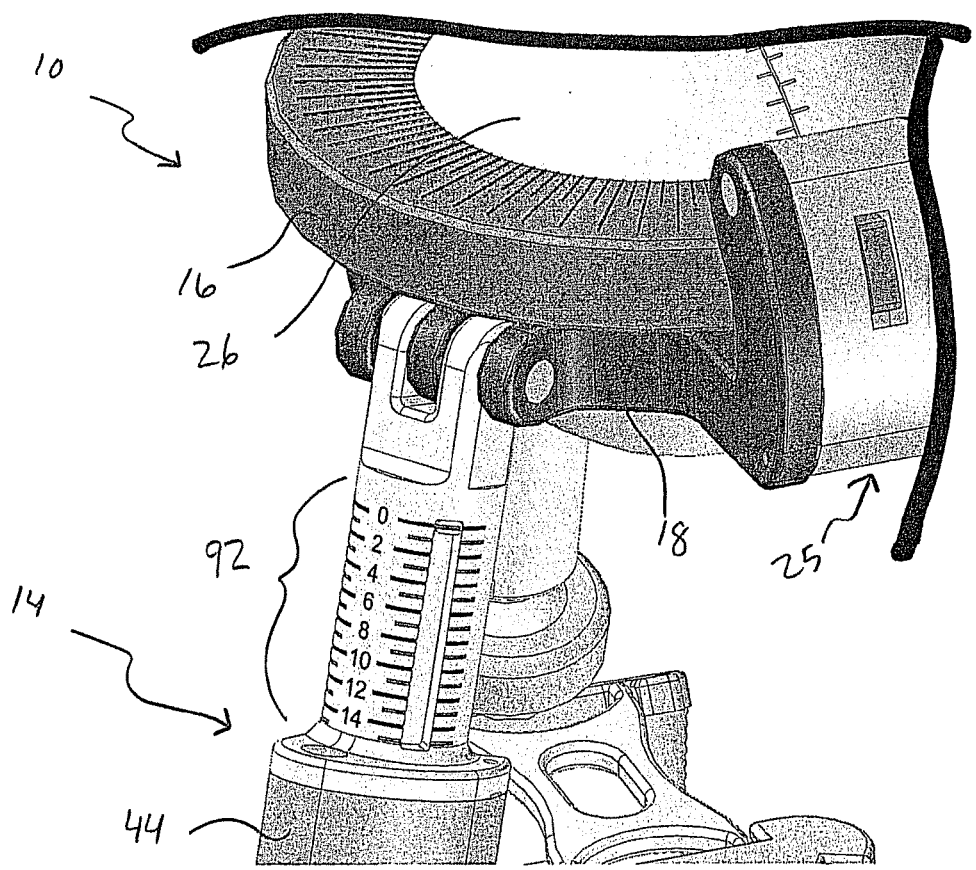
FIG. 8 illustrates a series of gradations printed on the telescoping leg to assist with setting a desired length of the leg.

Although not a necessary feature of the trajectory guide 10, each leg 14 may be printed with gradations 92 as illustrated in FIG. 8 which may assist the user to accurately set the desired length of the leg in a simple and quick manner. In one exemplary embodiment as illustrated in FIG. 8, the gradations 92 are printed in 1 mm increments and cover a range from 0 mm to 15 mm. This exemplary range corresponds with the 15 mm of linear leg travel as discussed above with reference to FIG. 6.

Figure 9:
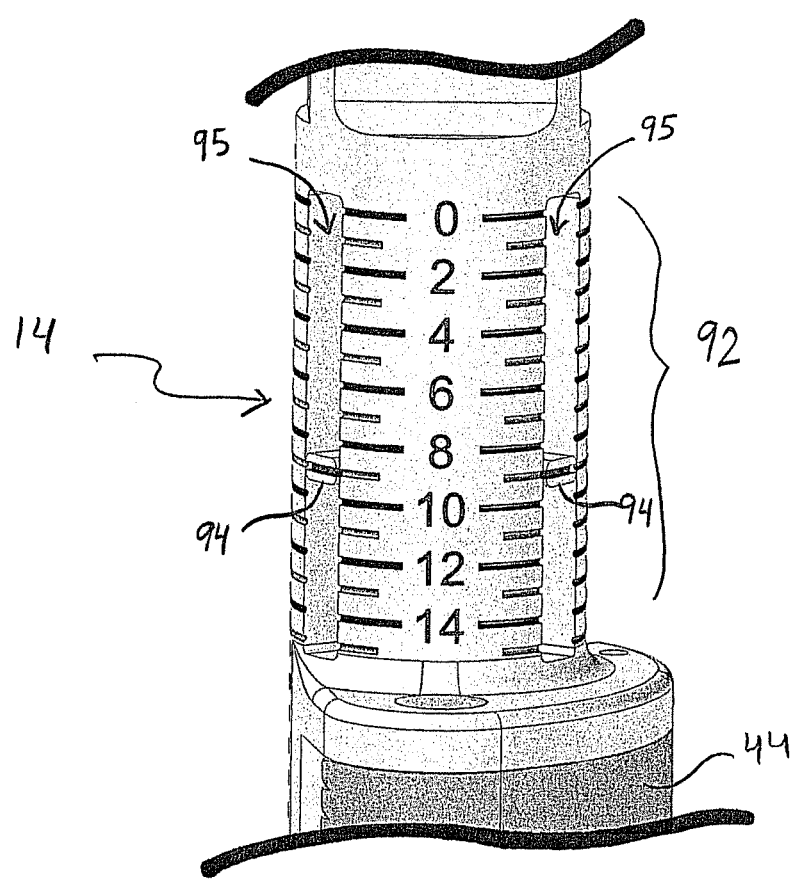
FIG. 9 is an enlarged view of the leg gradations of FIG. 8 illustrating a pair of alignment members coupled to the telescoping leg.

As illustrated in FIG. 9, one or more alignment members 94 may be positioned on the inner portion 64 of telescoping leg 14. The number of alignment members 94 may correspond with, for example, the number of alignment windows 95 formed adjacent to the gradations 92. In one exemplary embodiment, each alignment member 94 is in the form of a "pin" or post" and includes a printed line or marker which may be aligned with the gradations 92 on the outer portion 66 of the telescoping leg 14. Thus, by aligning the one or more alignment members 94 with the gradations 92, the user may visualize the amount that the corresponding leg 14 has been adjusted.

In addition to assisting with the length adjustment of the legs 14, the one or more alignment members 94 may also function as travel stops for the leg 14 to prevent the inner and outer portions 64 and 66 from becoming separated. In one exemplary embodiment as illustrated in FIG. 9, the alignment members 94 may be inserted through the windows 95 such that an end of the marker is substantially flush with the outer leg portion 66. Thus, when the inner leg portion is slid relative to the outer leg portion 66 such that the maximum leg length is achieved, the alignment members 94 may be designed such that they contact the lower end of the corresponding window 95 thereby preventing separation of the leg portions. Numerous other retention means for the leg portions are also possible as will be appreciated by those skilled in the art. For example, the telescoping leg 14 may include a pin or ball bearing member on one of the inner or outer leg portions 64 and 66 and a receiving well or aperture in the other of the inner or outer leg portions 64 and 66 that function together as a safety mechanism to prevent the leg portions from slidably disengaging during manipulation by the surgeon to set the trajectory.

Figure 10:
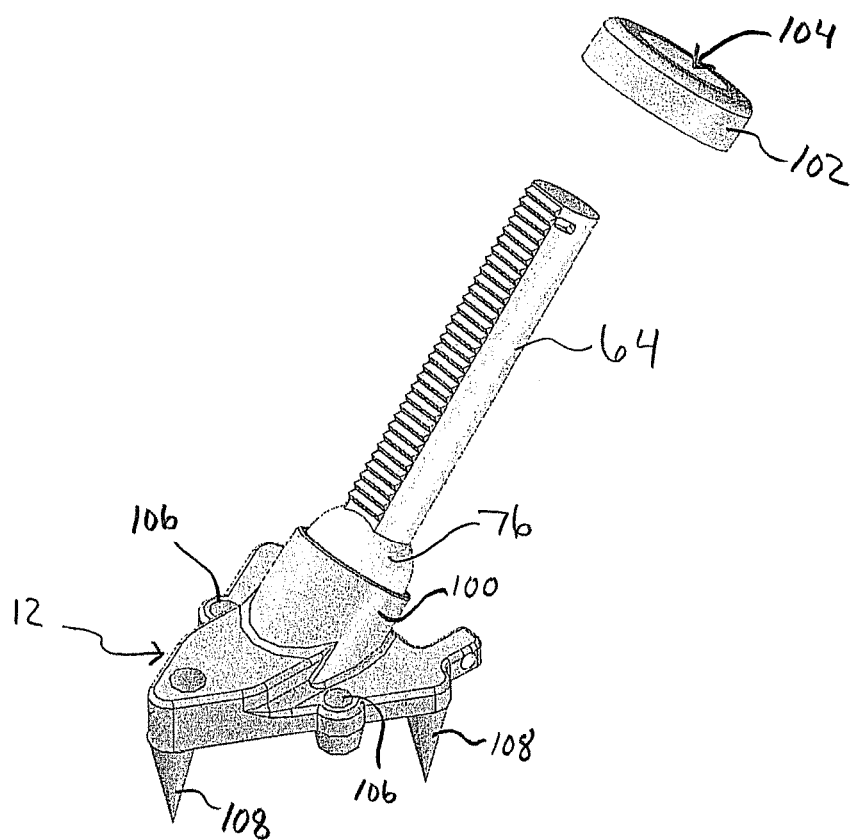
FIG. 10 is a perspective view of one foot of the trajectory guide engaging an inner portion of one of the telescoping legs.

As mentioned above, the trajectory guide 10 attaches to the skull with a plurality of feet 12 equal in number to the number of telescoping legs 14 to position the pivot point provided by the ball joint moveable member 26 above a surface of the skull. FIG. 10 is a perspective view of one of the feet 12 engaging the inner portion 64 of a corresponding telescoping leg 14. As illustrated in FIG. 10, each foot 12 includes a socket or sleeve portion 100 that is structured to house a lower portion of the ball joint 76 of the inner leg portion 64. A foot cap member 102 having an aperture 104 therethrough is structured to slide over the inner leg portion 64 and couple to the sleeve portion 100 in order to house an upper portion of the ball joint 76. Thus, the sleeve portion 100 and the foot cap member 104 function together to provide a ball joint retaining means. As will be appreciated by those skilled in the art, the foot cap member 102 may be coupled to the sleeve portion 100 via any suitable connection means including, but not limited to, with a press-fit type connection, a threaded connection (such that the foot cap member 102 is detachable from the sleeve portion 100), or with an adhesive.

As illustrated in FIG. 10, each foot may contain one or more apertures 106 structured for receiving bone screws or other fastening means. In one exemplary embodiment, the bone screws may be inserted into the apertures 106 and threaded into the patient's skull in order to secure each of the feet 12 in place. Optionally, each foot 12 may further include one or more sharp protrusions 108 extending from a bottom side of the foot that are structured to press into the scalp providing additional stability for the trajectory guide 10.

Figure 11:
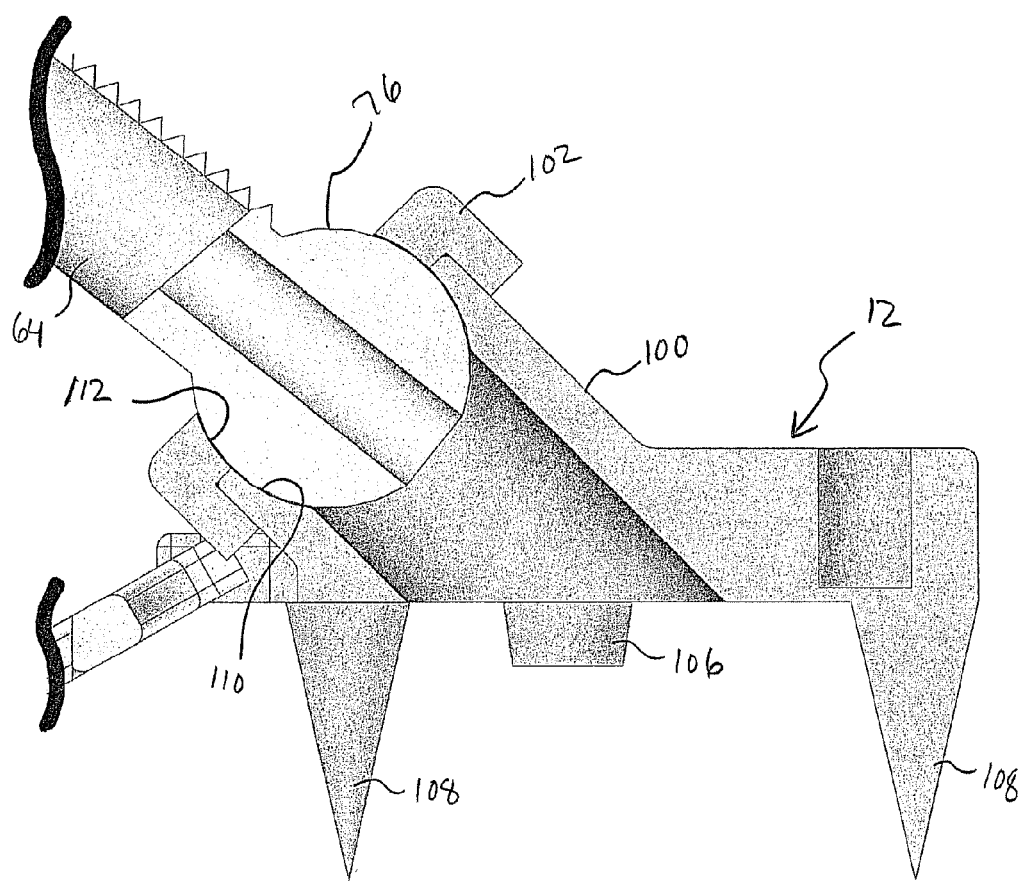
FIG. 11 is a cross-sectional view of a ball joint retaining means.

FIG. 11 is a cross-sectional view of the ball joint retaining means of FIG. 10. As illustrated in FIG. 11, the sleeve portion 100 and the foot cap member 102 include contoured inner surfaces 110 and 112, respectively, that are designed to allow the ball joint 76 to slide and rotate relative to the foot 12. Providing contoured inner surfaces 110 and 112 that have a curvature similar to the outer surface of the ball joint 76 reduces friction when adjusting the position of the telescoping leg 14 relative to the foot 12. Additionally, the clearances between the ball joint 76 and the contoured inner surfaces 110 and 112 are preferably sufficient to allow free movement of the ball joint, but minimized to prevent excess play between the components.

Figure 12:
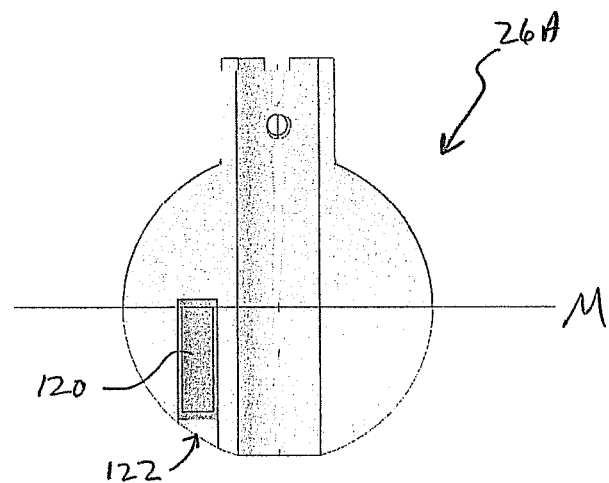
FIG. 12 is a cross-sectional view of one exemplary ball joint moveable member that includes a fiducial marker.
Figure 13:
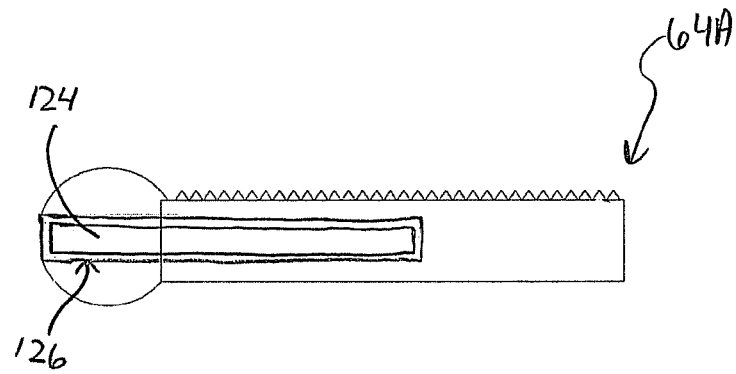
FIG. 13 is cross-sectional view of one exemplary lower leg portion of a telescoping leg that includes a fiducial marker.

When the trajectory guide in accordance with the present invention is used in combination with an imaging system, such as a Magnetic Resonance Imaging (MRI) system, it may be helpful to incorporate fiducial markers into the trajectory guide to provide points of reference for the user. FIGS. 12 and 13 illustrate two exemplary uses of fiducial markers in accordance with the present invention.

Particularly, FIG. 12 is a cross-sectional view of one exemplary ball joint moveable member 26A that includes a fiducial marker 120 positioned within a cutout 122 that may be seen in MRI scans. As illustrated in FIG. 12, the fiducial marker 120 may be inserted into the cutout 122 adjacent a bottom of the ball joint moveable member 26A such that an edge of the marker substantially aligns with a midline M of the ball. The fiducial marker 120 may then function to provide the exact location of the ball joint moveable member 26A in an MRI scan. The fiducial marker 120 may be held in place via any suitable connection means including, but not limited to, an adhesive or the like.

FIG. 13 is cross-sectional view of one exemplary inner leg portion 64A that includes a fiducial marker 124 positioned within a cutout 126 that may also be seen in MRI scans. As will be appreciated by those skilled in the art, each lower leg portion may be structured to receive a unique length, width, or shape of marker to enable the user to differentiate the legs in an MRI scan. Once again, the fiducial marker 124 may be held in place via any suitable connection means.

As will be appreciated by those skilled in the art, the placement of fiducial markers in the ball joint moveable member and the lower leg portion is illustrated merely for purposes of example and not limitation. Thus, fiducial markers may be positioned within various other components of the trajectory guide instead of or in addition to the ball joint moveable member and the lower leg portion without departing from the intended scope of the present invention.

Figure 14:
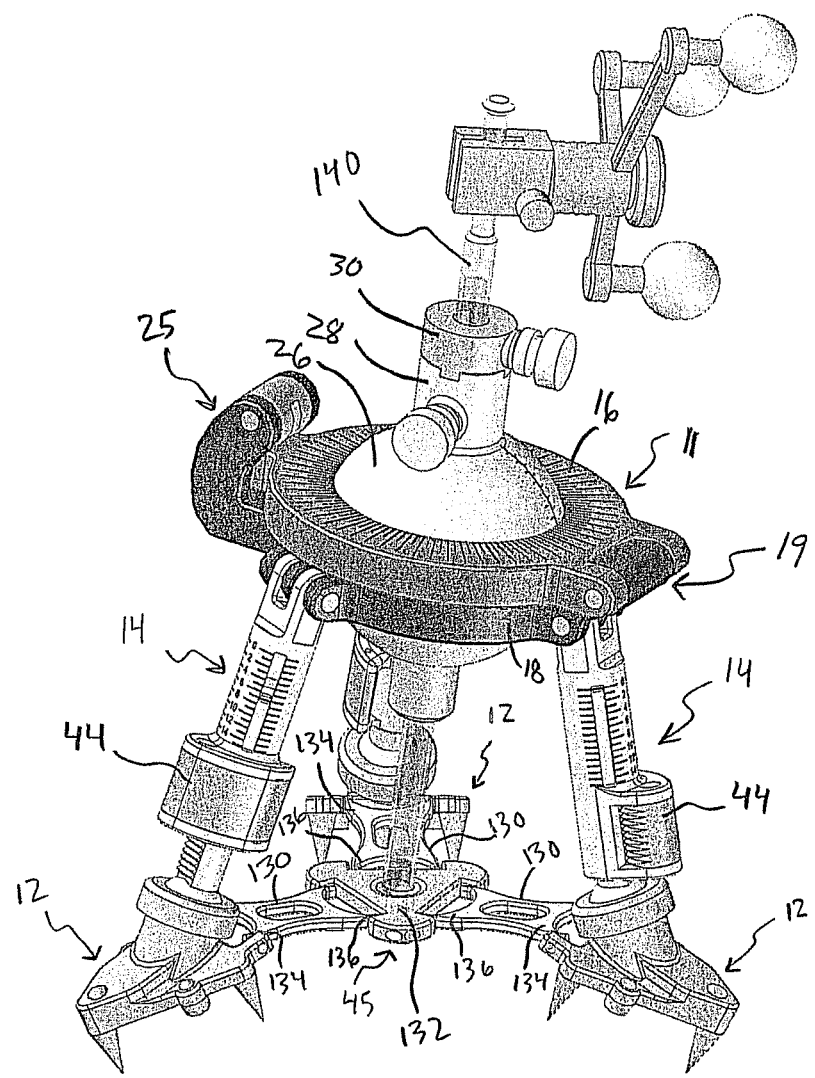
FIG. 14 is a perspective view detailing a web assembly coupled to the trajectory guide of FIG. 1.

Although the trajectory guide 10 has been illustrated herein as including the web assembly 45, as discussed above with reference to FIG. 1 the web assembly 45 is not a necessary component of the present invention and may be removed in alternative embodiments. However, for purposes of disclosure, one exemplary use of the web assembly 45 is illustrated in FIG. 14. Particularly, as shown in FIG. 14 each of the feet 12 may be connected to a web 130 of the web assembly 45, which may function to help ensure proper spacing and alignment of the legs 14 during placement on a patient. Each web 130 may in turn be connected to a single template center 132. The template center 132 may act as a connection for the webs 130 during the initial attachment of the trajectory guide 10 to the skull, which keeps the feet 12 properly spaced and aligned. Each of the webs 130 may be hingedly coupled on a first end 134 to the corresponding foot 12 and on a second end 136 to the template center 134. Providing such "dual hinged" webs 130 allow the feet 12 to tilt at various angles in order to follow the contours of the patient's head.

Figure 15:
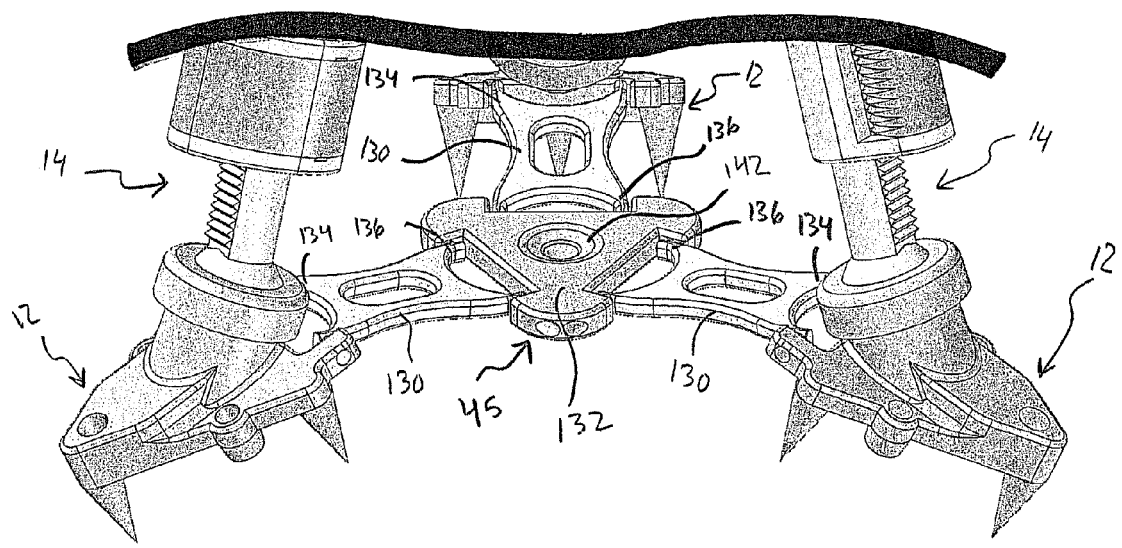
FIG. 15 illustrates the details of a template center portion of the web assembly of FIG. 14.

As illustrated in FIG. 14, the template center 132 may also be structured to function as a "stop" and/or a "pivot" for an instrument or tool, such as a trajectory tool 140. This may be achieved through a substantially round cutout 142 in a top side of the template center 132, as more clearly illustrated in FIG. 15. The trajectory tool 140 may pass through the center ball adapter 30 coupled to the adapter receiving member 28 of the ball joint moveable member 26 and rest within the cutout 142. As will be appreciated by those skilled in the art, the cutout 142 is structured and sized to allow free range of angular motion for the trajectory tool 140.

Figure 16:
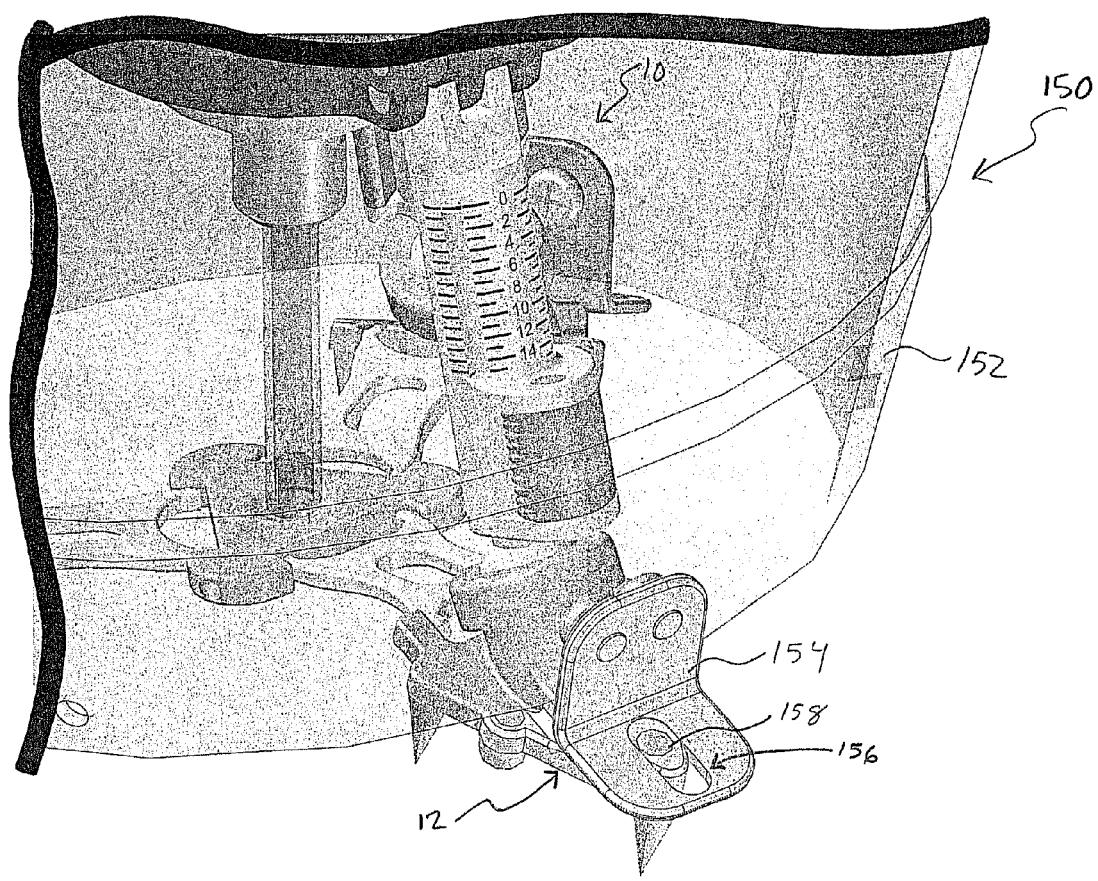
FIGS. 16-18 illustrate one exemplary protective cap and its method of attachment to a trajectory guide in accordance with the present invention.
Figure 17:
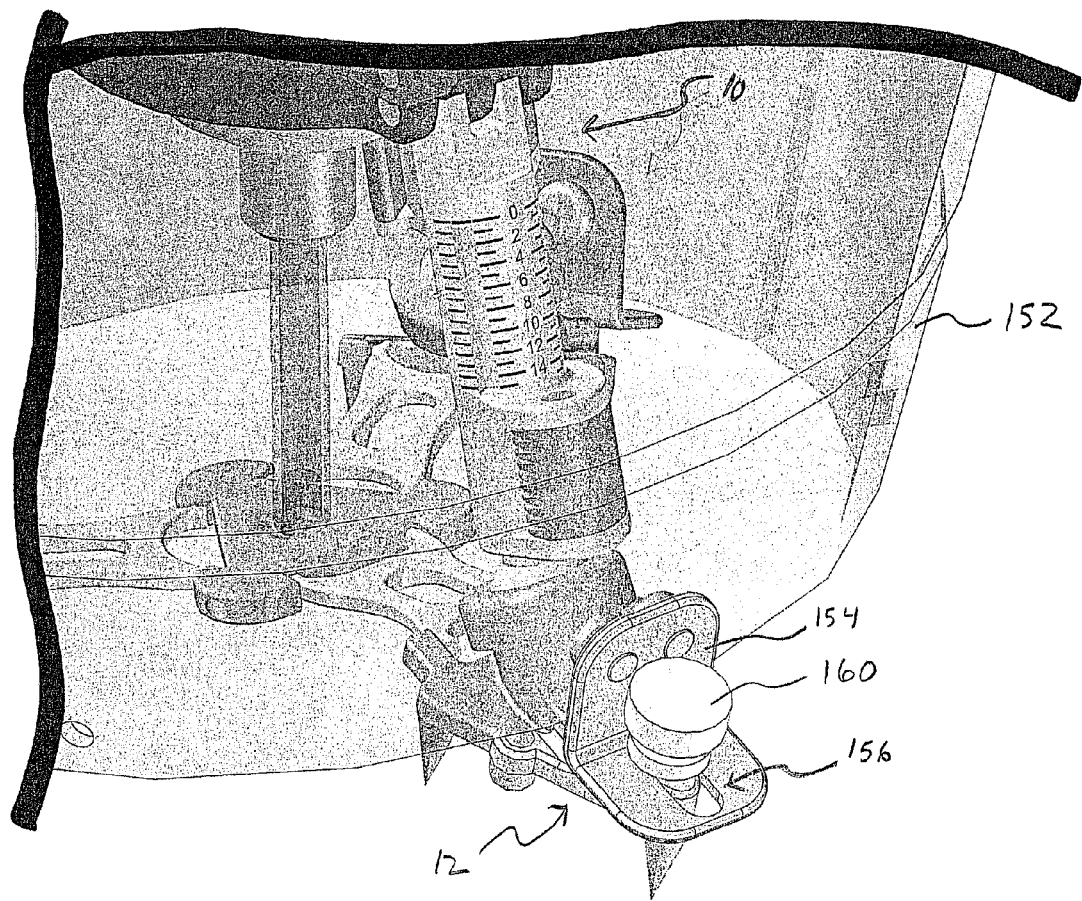
Figure 18:
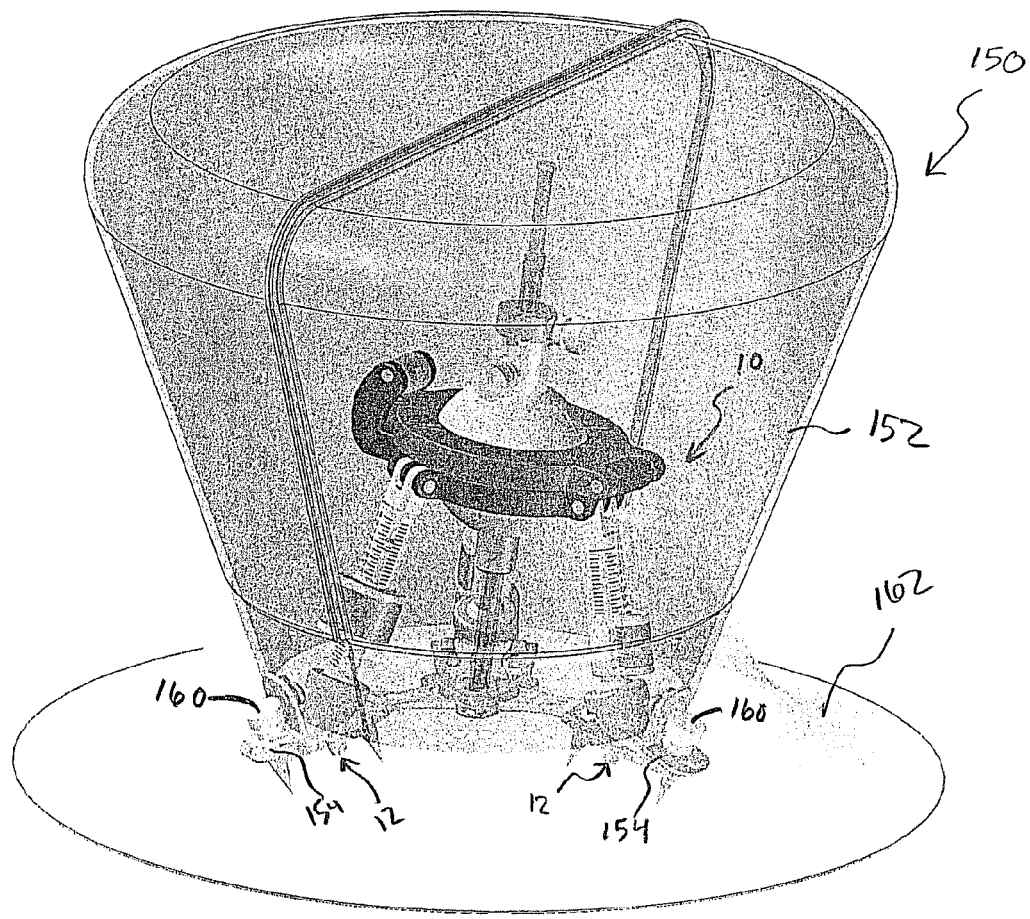

In a further embodiment of the present invention, once the trajectory guide 10 is attached to the patient and the trajectory is set, a protective cap may be attached to the trajectory guide to prevent accidental contact of the trajectory guide during, for example, patient transport to the MRI room. FIGS. 16-18 illustrate one exemplary protective cap 150 and its method of attachment. The protective cap 150 may be rigid and sized so as to accommodate any tool or instrument including, for example, an MRI wand and a trajectory tool interface. Furthermore, protective caps of various sizes may be provided to allow the user to select a cap that is appropriate for the type of tool or instrument currently positioned within the trajectory guide. As illustrated in FIG. 16, the protective cap 150 includes a main body 152 and a plurality of mounting tabs 154 (only one being shown) that correspond with the number of feet 12 of the trajectory guide. Each mounting tab 154 includes an opening 156 that may be aligned with an aperture 158 in the foot 12.

As illustrated in FIG. 17, a fastener 160 may be inserted through the opening 156 and into the aperture 158 in order to fasten each mounting tab 154 to the corresponding foot 12. In one exemplary embodiment the aperture 158 may be a threaded aperture and the fastener may be a threaded fastener, such as a plastic or metal thumb screw. However, any suitable fastening means may be utilized without departing from the intended scope of the present invention.

FIG. 18 is a perspective view of the protective cap 150 after attachment to the trajectory guide 10. As illustrated in FIG. 18, once the mounting tabs 154 have been fastened to the feet 12, a custom-fit drape 162 may be provided that wraps around the protective cap 150. The drape 162 may be structured and sized such that it hangs down from the protective cap 150 and conforms to the patient's head. The drape 162 may then be connected to the patient's head via any suitable attachment means to prevent unintentional movement of the drape As will be appreciated by those skilled in the art based upon the foregoing description with reference to the various figures, the trajectory guide in accordance with the present invention allows for any trajectory with respect to a target area. The maneuverability of the trajectory guide may allow a surgeon to drill and access multiple holes without having to move the position of the feet. Additionally, providing telescoping legs allows the surgeon to directly visualize the surgical site.

The foregoing description of the exemplary embodiments of the invention has been presented only for the purposes of illustration and description and is not intended to be exhaustive or to limit the invention to the precise forms disclosed. Many modifications and variations are possible in light of the above disclosure.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A trajectory guide comprising:
   a guide member;
   an assembly configured to hold the guide member such that the guide member pivots and rotates with respect to the assembly to obtain a plurality of pivot and rotation alignments between the guide member and the assembly;
   a lock coupled to the assembly configured to lock the guide member in a particular alignment of the plurality of pivot and rotation alignments;
   a plurality of legs coupled to the assembly configured to extend from the assembly and position the assembly and the guide member above a surface of a patient, such that a pivot point of the guide member is provided above the surface of the patient; and
   a trajectory tool configured to orient the guide member in a particular trajectory of a plurality of trajectories by concurrently controlling selection of: one of the plurality of pivot and rotation alignments between the guide member and the assembly, a pivot point alignment of a plurality of pivot point alignments between the assembly and a first end of at least one of the plurality of legs, one of a plurality of pivot and rotation alignments between each of a plurality of feet affixed to the surface of the patient and a corresponding second end of each of the plurality of legs, and an adjustment amount of an adjustable length of at least one of the plurality of legs.

2. The trajectory guide of claim 1, wherein the assembly is a ball-joint, where the guide member has a substantially ball shape, which is held between a first disk having a first hole and a second disk having a second hole included in the assembly.

3. The trajectory guide of claim 2, wherein the first disk is coupled to the second disk with a hinge joint.

4. The trajectory guide of claim 3, wherein:
   a lock includes a lock base that is fixed to the first disk and an adjustable lever that extends from the lock base, and the adjustable lever engages the second disk to squeeze the second disk towards the first disk in a locked position in which the guide member is locked in the particular alignment relative to the assembly, and the lever disengages the second disk in an unlocked position in which the guide member pivots and rotates with respect to the assembly.

5. The trajectory guide of claim 4, wherein each of the plurality of the legs is coupled to and extends from the first disk by a leg hinge joint.

6. The trajectory guide of claim 1, wherein the guide member includes a channel extending therethrough that coincides with the particular alignment.

7. The trajectory guide of claim 6, wherein the guide member includes a fastener at an end of the channel that is structured to fasten the guide member to an apparatus or device at an alignment that coincides with the particular alignment.

8. The trajectory guide of claim 1, wherein the at least one of the plurality of legs includes an adjustable portion that adjusts the adjustable length.

9. The trajectory guide of claim 8, wherein the adjustable portion is configured to adjust the adjustable length by sliding a first leg portion and a second leg portion relative to each other, the first leg portion and the second leg portion being included in the adjustable portion.

10. The trajectory guide of claim 9, wherein the second leg portion includes a channel structured to receive the first leg portion.

11. The trajectory guide of claim 8, wherein the at least one of the plurality of legs includes a leg lock configured to lock a position between first and second leg portions of the adjustable portion.

12. The trajectory guide of claim 11, wherein:
the leg lock includes a lock base that is fixed to the first leg portion and an adjustable lever that extends from the lock base,
the adjustable lever includes a plurality of teeth,
the teeth of the adjustable lever engage teeth of the second leg portion to lock the position between the first and second leg portions when the adjustable lever is in a locked position, and the teeth of the adjustable lever disengage the teeth of the second leg portion when the adjustable lever is in an unlocked position.

13. The trajectory guide of claim 1, wherein the plurality of feet are attached to the plurality of legs.

14. The trajectory guide of claim 13, wherein each of the plurality of legs includes a ball and each of the plurality of feet includes a cavity that receives the ball and forms a ball joint.

15. The trajectory guide of claim 14, wherein each of the plurality of feet includes a detachably attached foot cap that holds the ball in the cavity.

16. The trajectory guide of claim 1, wherein the plurality of legs are telescoping legs.

17. The trajectory guide of claim 1, wherein the trajectory guide is magnetic resonance imaging (MRI) compatible.

18. The trajectory guide of claim 17, further comprising:
one or more fiduciary markers that are visible in an MRI scan.

19. The trajectory guide of claim 18, wherein a first fiduciary marker of the fiduciary markers is provided in the guide member, the first fiduciary marker having a predefined shape that has a predefined relationship with the particular alignment, such that the particular alignment is discernable from the MRI scan via the first fiduciary marker.

20. A trajectory guide comprising:
guide means for guiding an instrument or an apparatus along a particular trajectory towards a target beneath a surface of a patient;
assembly means for holding the guide means and allowing the guide means to rotate and pivot in a plurality of pivot and rotation alignments, with respect to the assembly means;
locking means for locking the guide means in a particular alignment of the plurality of pivot and rotation alignments, the particular alignment being associated with the particular trajectory;
support means for supporting the assembly means and the guide means above the target and the surface of the patient, such that a pivot point of the guide means is provided above the surface of the patient; and
trajectory tool means for orienting the guide means in the particular trajectory of a plurality of trajectories by concurrently controlling selection of: one of the plurality of pivot and rotation alignments between the guide means and the assembly means, a pivot point alignment of a plurality of pivot point alignments between the assembly means and a first end of the support means, one of a plurality of pivot and rotation alignments between affixing means for affixing to the surface of the patient and a corresponding second end of the support means and, and an adjustment amount of an adjustable length of the support means.

21. A method for setting a trajectory of a trajectory guide, the trajectory guide comprising:
a guide member;
an assembly configured to hold the guide member such that the guide member pivots and rotates with respect to the assembly to obtain a plurality of pivot and rotation alignments between the guide member and the assembly;
a lock coupled to the assembly configured to lock the guide member in a particular alignment of the plurality of pivot and rotation alignments;
a plurality of legs coupled to the assembly configured to extend from the assembly and position the assembly and the guide member above a surface of a patient, such that a pivot point of the guide member is provided above the surface of the patient; and
a trajectory tool configured to orient the guide member in a particular trajectory of a plurality of trajectories,
the method comprising:
obtaining the particular trajectory by concurrently controlling, by the trajectory tool, selection of: one of the plurality of pivot and rotation alignments between the guide member and the assembly, a pivot point alignment of a plurality of pivot point alignments between the assembly and a first end of at least one of the plurality of legs, one of a plurality of pivot and rotation alignments between each of a plurality of feet affixed to the surface of the patient and a corresponding second end of each of the plurality of legs, and an adjustment amount of an adjustable length of at least one of the plurality of legs.

22. The method according to claim 21, further comprising:
attaching an apparatus or device to the guide member such that the attached apparatus or device is introduced to the patient at the surface of the patent in accordance with the particular trajectory.

* * * * *